US008021666B2

(12) United States Patent
Palomba et al.

(10) Patent No.: US 8,021,666 B2
(45) Date of Patent: *Sep. 20, 2011

(54) METHOD AND COMPOSITIONS FOR STIMULATION OF AN IMMUNE RESPONSE TO CD20 USING A XENOGENEIC CD20 ANTIGEN

(75) Inventors: Maria Lia Palomba, New York, NY (US); Alan Houghton, New York, NY (US); Jedd Wolchok, New York, NY (US); David A. Scheinberg, New York, NY (US); Wendy K. Roberts, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 2280 days.

This patent is subject to a terminal disclaimer.

(21) Appl. No.: 10/285,874

(22) Filed: Oct. 31, 2002

(65) Prior Publication Data

US 2003/0228326 A1 Dec. 11, 2003

Related U.S. Application Data

(63) Continuation-in-part of application No. 09/627,694, filed on Jul. 28, 2000, now abandoned, which is a continuation-in-part of application No. 09/308,697, filed as application No. PCT/US97/22669 on Dec. 10, 1997, now Pat. No. 6,328,969.

(60) Provisional application No. 60/036,419, filed on Feb. 18, 1997.

(51) Int. Cl.
C07K 14/705 (2006.01)
C07K 14/435 (2006.01)
A61K 39/00 (2006.01)

(52) U.S. Cl. ............... 424/185.1; 424/450; 424/85.1

(58) Field of Classification Search ............... 424/185.1, 424/450, 85.1
See application file for complete search history.

(56) References Cited

U.S. PATENT DOCUMENTS

| 5,262,177 | A | 11/1993 | Brown et al. | |
| 5,314,813 | A | 5/1994 | Peterson et al. | |
| 5,397,703 | A | 3/1995 | De Boer et al. | |
| 6,328,969 | B1 | 12/2001 | Houghton et al. | |
| 7,556,805 | B2 * | 7/2009 | Houghton et al. | 424/184.1 |
| 2002/0155093 | A1 * | 10/2002 | Houghton et al. | 424/184.1 |

FOREIGN PATENT DOCUMENTS

| WO | WO 92/17205 | 10/1992 |
| WO | WO 98/04720 | 2/1998 |
| WO | WO 98/25574 | 6/1998 |

OTHER PUBLICATIONS

Haupt et al (Exp Biol Med 227(4):227-237 (2002)).*
Nettlebeck et al. (TIG 16(4):174-181 (Apr. 2000)).*
Niemann (Transgenic research 7:73-75 (1998)).*
Bowne et al. (J. Exp. Med. 190:1717-1722 (Dec. 6, 1999)).*
You et al (Cancer Research, 61:3704-3711 (2001).*
Tedder et al. (J. Immunol. 141:4388-4394 (1988)).*
Mahoto et al (J. Drug Targeting, 4(6):337-357 (1997).*
Bronte Current Gene Therapy 1:53-100 (2001).*
Roberts et al. Blood 99(10):3748-3755 (May 15, 2002).*
Ochiai et al. Leukemia & Lymphoma, 46(11):1619-1625 (2005).*
Tedder et al. (1989) J. lmmunol. 142:2560-2568.*
Tedder et al. (1988) J. Immunol. 141:4388-4394.*
Stamenkovic et al. (1988) J. Exp. Med. 167:1975-1980.*
Einfeld et al. (1988) EMBO J. 7:711-717.*
Tedder et al. (1988) PNAS 85:208-212.*
Maloney et al. (Blood 90(6):2188-2195 (Sep. 15, 1997).*
Press et al. (Blood 69(2):584-591 (1987)).*
Fang et al. (Can. Research 65(20):9328-9337 (2005)).*
Patent Application Data Sheet (U.S. Patent No. 7556805 (U.S. Appl. No. 09/996,128)), filed Jun. 7, 2010; pp. 1-2).*
B. Bouchard et al., "Induction of Pigmentation in Mouse Fibroblasts by Expression of Human Tyrosinase cDNA", *J. Exp. Med.*, 1989, vol. 169, pp. 2029-2042.
B. Bouchard et al., "Production and Characterization of Antibodies against Human Tyrosinase", *The Journal of Investigative Dermatology*, 1994, vol. 102, No. 3, pp. 291-295.
J. Rowell et al., "Lysosome-Associated Membrane Protein-1-Mediated Targeting of the HIV-1 Envelope Protein to an Endosomal/Lysosomal Compartment Enhances Its Presentation to MHC Class II-Restricted T Cells", *The American Association of Immunologists*, 1995, pp. 1818-1828.
S. Krishnan et al., "Paving the way towards DNA vaccines", *Nature Medicine*, 1995, vol. 1, No. 6, pp. 521-522.
S. Barclay et al., "Rapid isolation of monoclonal antibodies specific for cell surface differentiation antigens", *Proc. Natl. Acad. Sci. USA*, 1986 vol. 83, pp. 4336-4340.
S. Vijayasaradhi et al., "Intracellular Sorting and Targeting of Melanosomal Membrane Proteins: Identification of Signals for Sorting of the Human Brown Locus Protein, GP75", *The Journal of Cell Biology*, 1995, vol. 130, No. 4, pp. 807-820.
D. Pardon et al., "Exposing the Immunology of Naked DNA Vaccines", *Immunity*, Cell Press, 1995, vol. 3, pp. 165-169.
S. Vijayasaradhi et al., "The Melanoma Antigen gp75 is the Human Homologue of the Mouse b (Brown) Locus Gene Product", *J. Exp. Med*, 1990, vol. 171, pp. 1375-1380.

(Continued)

*Primary Examiner* — Lynn Bristol
(74) *Attorney, Agent, or Firm* — Larson & Anderson, LLC

(57) ABSTRACT

Tolerance of the immune system for endogenous CD20 can be overcome and an immune response stimulated by administration of xenogeneic or xenoexpressed CD20 antigen. For example, mouse CD20, or antigenically-effective portions thereof, can be used to stimulate an immune response to the corresponding differentiation antigen in a human subject. Administration of xenogeneic antigens in accordance with the invention results in an effective immunity against CD20 expressed by the cancer in the treated individual, thus providing a therapeutic approach to the treatment of lymphomas and leukemia expressing CD20.

21 Claims, 9 Drawing Sheets

OTHER PUBLICATIONS

G. Adema et al., "Molecular Characterization of the Melanocyte Lineage-specific Antigen gp100", *The Journal of Biology Chemistry*, The American Society for Biochemistry and Molecular Biology, 1994, vol. 269, No. 31, pp. 20126-20133.

A. Houghton et al., "Recognition of Autoantigens by Patients with Melanoma", *Annals New York Academy of Sciences*, 1993, pp. 59-69.

C. Naftzger et al., "Immune response to a differentiation antigen induced by altered antigen: A study of tumor rejection and autoimmunity", *Proc. Natl. Acad. Sci. USA*, 1996, vol. 93, pp. 14809-14814.

F. Ausubel et al., "Expression of Proteins in Insect Cells using Baculoviral Vectors", *Current Protocols in Molecular Biology*, Greene Publishing and Wiley-Interscience, 1990, vol. 8, 16.8.1-16.11.7.

J. Ulmer et al., "Heterologous Protection Against Influenza by Injection of DNA Encoding a Viral Protein", Science, 1993, vol. 259, pp. 1745-1749.

C. Tiffs et al., "The Folding and Cell Surface Expression of CD4 Requires Glycosylation", *The Journal of Biological Chemistry*, 1992, vol. 267, No. 5, pp. 3268-3273.

S. Park, "JL1, a Novel Differentiation Antigen of Human Cortical Thymocyte", *J Exp. Med.*, The Rockefeller University Press, 1993, vol. 178, pp. 1447-1451.

C. Cabañas et al., "Characterization of a CD11c-Reactive Monoclonal Antibody (HC1/1) Obtained by Immunizing with Phorbol Ester Differentiated U937 Cells", *Hybridoma*, 1988, vol. 7, No. 2, pp. 167-177.

N. Nanda et al., "Induction of Anti-Self-Immunity to Cure Cancer", *Cell*, 1995, vol. 82, pp. 13-17.

* cited by examiner

METHOD AND COMPOSITIONS FOR STIMULATION OF AN IMMUNE RESPONSE TO CD20 USING A XENOGENEIC CD20 ANTIGEN

This application is a continuation-in-part of U.S. patent application Ser. No. 09/627,694, filed Jul. 28, 2000, and now abandoned, which is continuation-in-part of U.S. patent application Ser. No. 09/308,697, filed May 21, 1999, now U.S. Pat. No. 6,328,969, which is a §371 National Phase of International Application No. PCT/US97/22669 filed Dec. 10, 1997. PCT/US97/22669 claims benefit under 35 USC §119(e) of US Provisional Application No. 60/036,419 filed Feb. 18, 1997. All of the aforementioned applications are incorporated herein reference.

FIELD OF THE INVENTION

This application relates to a method and compositions for stimulation of an immune response to CD20.

BACKGROUND OF THE INVENTION

Most tumor immunity is mediated by recognition of self-antigens, antigens present in cancer cells that are also found in normal host tissue. Houghton, A. N., *J. Exp. Med.* 180: 1-4 (1994). This type of immunity is more akin to autoimmunity than to immunity in infectious diseases, where the response is directed at a truly foreign antigen, present in the pathogen but not in host tissue. Evidence of this can be found in the autoimmune sequelae that often follow the development of successful tumor immunity. Bowne, W. B., et al., *J. Exp. Med.* 190 (11):1717-1722 (1999).

Differentiation antigens form one prototype of self-antigens in cancer immunity. Houghton, A. N., et al., *J. Exp. Med.* 156(6):1755-1766 (1982). Differentiation antigens are tissue-specific antigens that are shared by autologous and some allogeneic tumors of similar derivation, and on normal tissue counterparts at the same stage of differentiation. Differentiation antigens have been shown to be expressed by a variety of tumor types, including melanoma, leukemia, lymphomas, colorectal, carcinoma, breast carcinoma, prostate carcinoma, ovarian carcinoma, pancreas carcinomas, and lung cancers. Typically the expression of these antigens changes as a cell matures and can characterize tumors as more or less differentiated. For example, differentiation antigens expressed by melanoma cells include Melan-A/MART-1, Pmel17, tyrosinase, gp75 and gp100. Differentiation antigens expressed by lymphomas and leukemia include CD19 and CD20/CD20 B lymphocyte differentiation markers. An example of a differentiation antigen expressed by colorectal carcinoma, breast carcinoma, pancreas carcinoma, prostate carcinoma, ovarian carcinoma, and lung carcinoma is the mucin polypeptide muc-1. A differentiation antigen expressed by breast carcinoma is her2/neu. The her2/neu differentiation antigen is also expressed by ovarian carcinoma. Differentiation antigens expressed by prostate carcinoma include prostate specific antigen, prostatic acid phosphatase, and prostate specific membrane antigen (PSMA).

Unfortunately, in most cases, the immune system of the individual is tolerant of these antigens, and fails to mount an effective immune response. For the treatment of cancers where the tumor expresses differentiation antigens therefore, it would be desirable to have a method for stimulating an immune response against the differentiation antigen in vivo. It is an object of the present invention to provide such a method.

SUMMARY OF THE INVENTION

It has now been found that the tolerance of the immune system for endogenous CD20 can be overcome and an immune response stimulated by administration of xenogeneic CD20 and CD20 (including syngeneic CD20) expressed in cells of different species. For example, mouse CD20, or antigenically effective portions thereof, can be used to stimulate an immune response to the corresponding differentiation antigen in a human subject. Administration of xenogeneic or xenoexpressed antigens in accordance with the invention results in an effective immunity against CD20 expressed by the cancer in the treated individual, thus providing a therapeutic approach to the treatment of lymphomas and leukemia expressing CD20.

DETAILED DESCRIPTION OF THE INVENTION

Figure 1A:
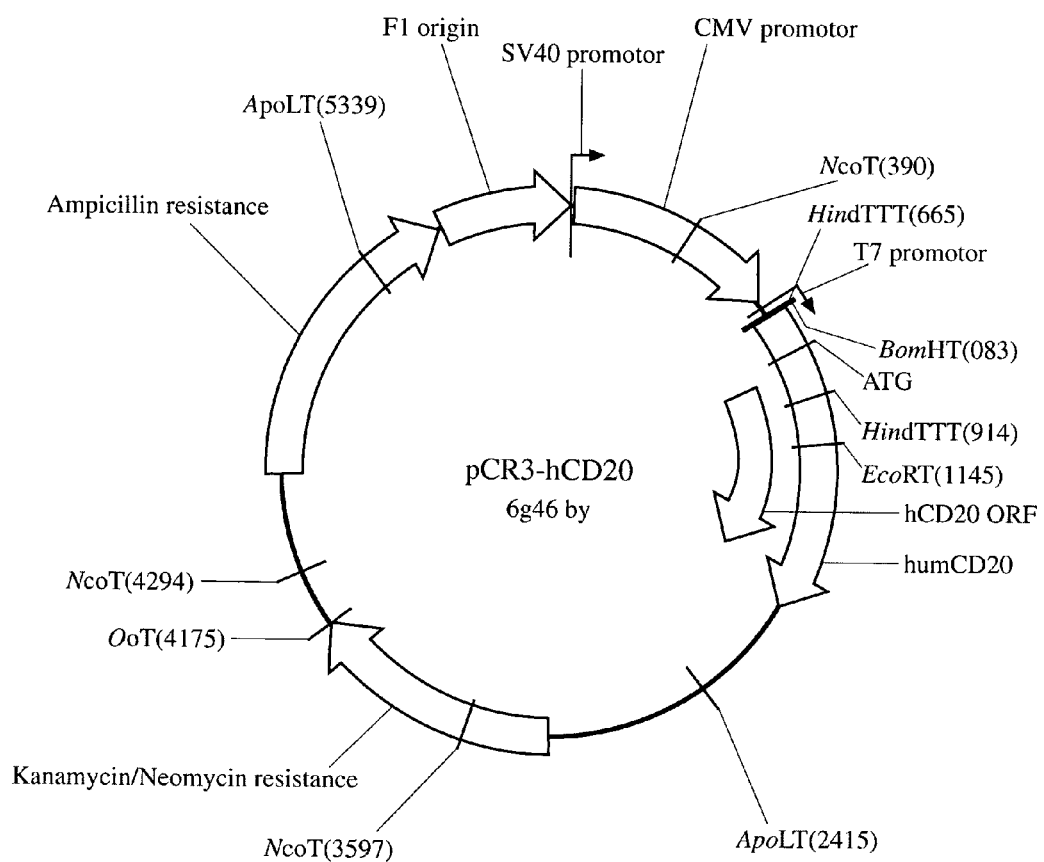
FIGS. 1a-d show the maps of four plasmids containing regions encoding a CD20 antigen.
Figure 1B:
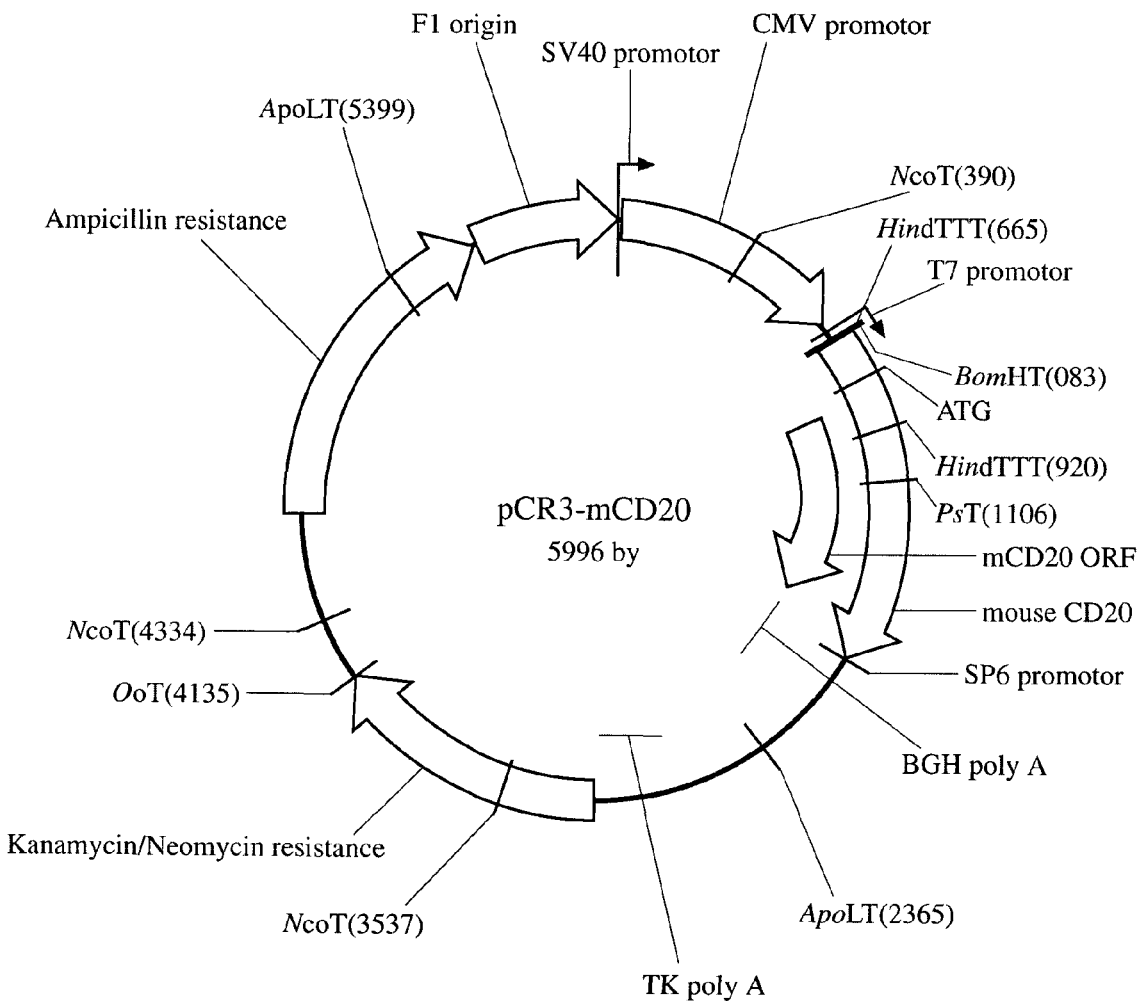

The present invention provides a method for stimulating an immune response to a tissue expressing CD20 in a subject individual. The subject individual is preferably human, although the invention can be applied in veterinary applications to animal species, preferably mammalian (for example horse, dog or cat) or avian species, as well.

As used in the specification and claims of this application, the term "immune response" encompasses both cellular and humoral immune responses. Preferably, the immune response is sufficient to provide immunoprotection against growth of tumors expressing CD20. The term "stimulate" refers to the initial stimulation of a new immune response or to the enhancement of a pre-existing immune response.

In accordance with the invention, a subject individual is treated to stimulate an immune response to endogenous CD20 by administering a xenogeneic or xenoexpressed CD20 antigen. The term "xenogeneic" denotes the fact that the administered antigen has a sequence peptide different from the CD20 of the species being treated and originates from a different species. For treatments of humans, preferred xenogeneic antigens will be rodent antigens, for example mouse, but could come from other mammals such as dog, cat, cow, or sheep, or from birds, fish, amphibian, reptile, insect or other more distantly related species. The term "xenoexpressed" refers to an antigen which may be syngeneic with the subject individual, but which is expressed in cells of a species different from the subject individual, for example in insect cells.

The term "CD20 antigen" refers to a protein/peptide antigen or to a polynucleotide having a sequence that is expressed in vivo to produce the protein/peptide antigen. In either case, the protein/peptide antigen may be the entire CD20 molecule, or some antigenic portion thereof derived from the extracellular domain. For example, as described below, plasmids were prepared using either full length cDNA or using a portion encoding a 43 amino acid extracellular loop (amino acids 136-179 in the mouse protein; amino acids 142-185 in the human protein).

Administration of a protein/peptide xenogeneic or xenoexpressed CD20 antigen can be accomplished by several routes. First, the xenogeneic CD20 may be administered as part of a vaccine composition which may include one or more adjuvants such as alum, QS21, TITERMAX or its derivatives, incomplete or complete Freund's and related adjuvants, and cytokines such as granulocyte-macrophage colony stimulating factor (GM-CSF), flt-3 ligand, interleukin-2, interleukin-4 and interleukin-12 for increasing the intensity of the immune response. The vaccine composition may be in the form of xenogeneic CD20 antigen in a solution or a suspension, or the therapeutic differentiation antigen may be introduced in a lipid carrier such as a liposome. Such compositions will generally be administered by subcutaneous, intradermal or intramuscular route. Vaccine compositions containing protein/peptide xenogeneic or xenoexpressed CD20 antigen are administered in amounts which are effective to stimulate an immune response to the target differentiation antigen in the subject individual. The preferred amount to be administered will depend on the species of the target individual and on the specific antigen, but can be determined through routine preliminary tests in which increasing doses are given and the extent of antibody formation or T cell response is measured by enzyme-linked immunosorbent assay (ELISA) or similar tests. T cell responses may also be measured by cellular immune assays, such as cytokine release assays and proliferation assays.

Xenogeneic CD20 antigen may also be introduced in accordance with the invention using a DNA immunization technique in which DNA encoding the antigen is introduced into the subject such that the antigen is expressed by the subject. Xenogeneic CD20 antigen may also be administered as a purified protein. Proteins can be purified for this purpose from cell lysates using column chromatography procedures. Proteins for this purpose may also be purified from recombinant sources, such as bacterial or yeast clones or mammalian or insect cell lines expressing the desired product.

Xenogeneic CD20 antigen may also be administered indirectly through genetic immunization of the subject with DNA encoding the antigen. cDNA encoding the xenogeneic CD20 antigen is combined with a promoter which is effective for expression of the cDNA in mammalian cells. This can be accomplished by digesting the nucleic acid polymer with a restriction endonuclease and cloning into a plasmid containing a promoter such as the SV40 promoter, the cytomegalovirus (CMV) promoter or the Rous sarcoma virus (RSV) promoter. The resulting construct is then used as a vaccine for genetic immunization. The cDNA can also be cloned into plasmid and viral vectors that are known to transduce mammalian cells. These vectors include retroviral vectors, adenovirus vectors, vaccinia virus vectors, pox virus vectors and adenovirus-associated vectors.

FIGS. 1a-d show maps of four plasmids containing regions encoding a CD20 antigen: pCR3-mCD20, pCR3-hCD20, pNERIS-M8, and pNERIS-H8. The preparation and use of these plasmids is described in the examples below.

The nucleic acid constructs containing the promoter, CD20 antigen-coding region and intracellular sorting region can be administered directly or they can be packaged in liposomes or coated onto colloidal gold particles prior to administration. Techniques for packaging DNA vaccines into liposomes are known in the art, for example from Murray, ed. "Gene Transfer and Expression Protocols" Humana Pres, Clifton, N.J. (1991). Similarly, techniques for coating naked DNA onto gold particles are taught in Yang, "Gene transfer into mammalian somatic cells in vivo", *Crit. Rev. Biotech.* 12: 335-356 (1992), and techniques for expression of proteins using viral vectors are found in Adolph, K. ed. "Viral Genome Methods" CRC Press, Florida (1996).

For genetic immunization, the vaccine compositions are preferably administered intradermally, subcutaneously or intramuscularly by injection or by gas driven particle bombardment, and are delivered in an amount effective to stimulate an immune response in the host organism. The compositions may also be administered ex vivo to blood or bone marrow-derived cells (which include APCs) using liposomal transfection, particle bombardment or viral infection (including co-cultivation techniques). The treated cells are then reintroduced back into the subject to be immunized. While it will be understood that the amount of material needed will depend on the immunogenicity of each individual construct and cannot be predicted a priori, the process of determining the appropriate dosage for any given construct is straightforward. Specifically, a series of dosages of increasing size, starting at about 0.1 µg is administered and the resulting immune response is observed, for example by measuring antibody titer using an ELISA assay, detecting CTL response using a chromium release assay or detecting TH (helper T cell) response using a cytokine release assay.

In the experiments described below, the BALB/c mouse lymphoma model, in which the mouse lymphoma cell line A20 is used to challenge the animals after immunization with CD20, was used to test the efficacy of treatment. The intravenous injection of $5 \times 10^4$ A20 cells in non-immunized mice results in the development in 3 to 4 weeks of ascites and large palpable tumor masses in the abdomen. This is usually accompanied by weight gain. A few mice develop hind-legs paralysis and wasting. In our studies, groups of 10-12 mice received five weekly immunizations with either the vector alone (pCR3) or one of the following: pCR3-mCD20, pCR3-hCD20, pNERIS-M8 or pNERIS-H8. The latter two plasmids encode for a 43 aa extracellular loop (aa 136-179 in the mouse protein and 142-185 in the human protein). The vaccinations were tolerated without any appreciable side effects other than minimal inflammation of the skin at the site of inoculation. Five days following the last immunization, the mice were challenged with $5 \times 10^4$ A20 cells. The first signs of tumor development were observed as expected around the third week after tumor challenge. Results are plotted as Kaplan-Meier survival curves in FIGS. 2a-d. The groups were compared by log rank test. Mice vaccinated with the vector control plasmid (pCR3) and the full-length mouse cDNA (pCR3-mCD20) developed ascites and tumor masses at a similar pace, and had to be sacrificed between 34 and 45 days post-challenge in three independent experiments. Mice immunized with the human minigene (pNERIS-H8) displayed a slower pace of tumor take, as shown in panel 3a and 3b. Long-term survival, defined as survival up to 60 days post-challenge, was modestly but statistically better in mice immunized with pCR3-H8 (3d and 3d, p<0.05 in both cases). Results in mice immunized with the full-length human cDNA (pCR3-hCD20) or the mouse minigene (pNERIS-M8) were more variable, and not statistically significant. These results were consistently reproduced three times.

Figure 3:
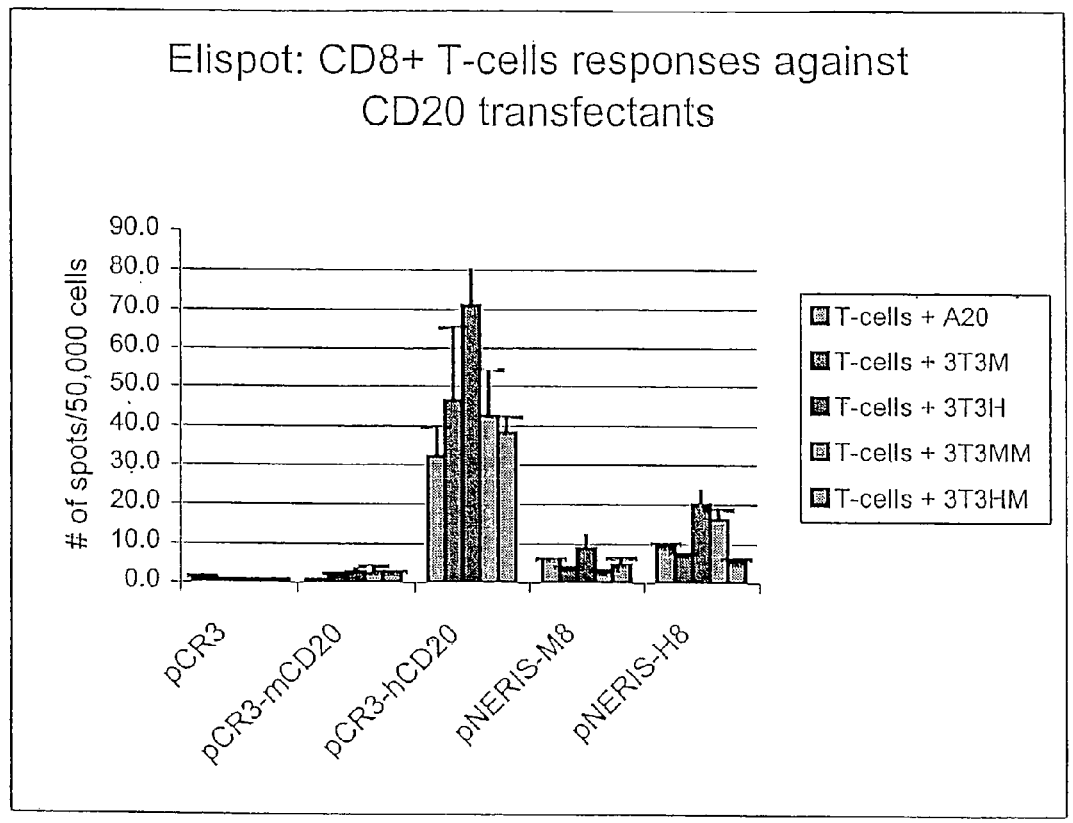
FIG. 3 shows T cell responses against CD20 in mice immunized with CD20.

T-cell responses against mouse CD20 were observed following vaccination with human CD20 DNA. BALB/c-3T3 fibroblasts were stably transfected with the plasmids expressing full-length human and mouse CD20 (3T3H and 3T3M, respectively) and human and mouse minigenes (3T3HM and 3T3MM), as described. CD8+ T-cells were isolated by positive selection from mice immunized weekly three times with the same constructs. The T-cells were tested for reactivity against each antigen by elispot assay as described in the examples. As shown in FIG. 3, T-cells from mice immunized with pCR3 only did not react against any of the transfectants. Mice immunized with both the full-length mouse CD20 and the mouse minigene had also a background reactivity. The CD8+ T-cells of mice immunized with the human full-length CD20 reacted strongly against not only 3T3H but also with 3T3M, 3T3HM and 3T3MM, as well as against A20, a CD20-expressing cell line. Mice immunized with the human minigene had intermediate responses, with significant reactivity against 3T3H and 3T3MM.

Antibody responses against mouse CD20 were observed following vaccination with human CD20 DNA. The sera of the immunized mice was collected and analyzed for the presence of anti-mouse CD20 antibodies, a sign of autoimmunity. The sera were immuno-precipitated with recombinant mCD20 protein in the presence of anti-mouse IgG bound to agarose beads. Negative controls for non-specific binding of the anti-mouse IgG did not include recombinant CD20 in the reaction. The precipitated proteins, separated in a 4-20% SDS-PAGE were then blotted with the monoclonal antibody anti-Xpress. The expected size of the recombinant mCD20 is 40Kda. In the sera from mice immunized with syngeneic DNA we could not detect any anti-CD20 antibodies, while four out of five mice immunized with xenogeneic DNA display the presence of auto-reactive anti CD20 antibodies. Analysis of the sera from mice immunized with both human and mouse minigenes revealed the presence of anti CD20 antibodies in about 80% of the animals tested.

In accordance with a further aspect of the present invention, an immune response against a target differentiation antigen can be stimulated by the administration of syngeneic differentiation antigen expressed in cells of a different species, i.e. by xeonexpressed CD20 antigen. In general, the subject being treated will be a human or other mammal. Thus, insect cells are a preferred type of cells for expression of the syngeneic differentiation antigen. Suitable insect cell lines includes Sf9 cells and Schneider 2 Drosophila cells. The therapeutic differentiation antigen could also be expressed in bacteria, yeast or mammalian cell lines such as COS or Chinese hamster ovary cells. Host cells which are evolutionarily remote from the subject being treated, e.g. insects, yeast or bacteria for a mammalian subject, may be preferred since they are less likely to process the expressed protein in a manner identical to the subject.

To provide for expression of the differentiation antigen in the chosen system, DNA encoding the differentiation antigen or a portion thereof sufficient to provide an immunologically effective expression product is inserted into a suitable expression vector. There are many vector systems known which provide for expression of incorporated genetic material in a host cell, including baculovirus vectors for use with insect cells, bacterial and yeast expression vectors, and plasmid vectors (such as psvk3) for use with mammalian cells. The use of these systems is well known in the art. For treatment of humans with a syngeneic differentiation antigen, cDNA encoding the human differentiation antigen to be targeted must be available. cDNA is produced by reverse transcription of mRNA, and the specific cDNA encoding the target differentiation antigen can be identified from a human cDNA library using probes derived from the protein sequence of the differentiation antigen. The cDNA sequences human CD20 is known, and is reflected in the sequences provided herein. Xenoexpressed CD20 antigen, like purified xenogeneic CD20 antigen, is administered to the subject individual in an amount effective to induce an immune response. The composition administered may be a lysate of cells expressing the xenoexpressed antigen, or it may be a purified or partially purified preparation of the xenoexpressed antigen.

The invention will now be further described with reference to the following, non-limiting examples, in which the following material were used:

Mice: BALB/c mice were purchased from the National Cancer Institute breeding program (Frederick, Md.) or from Taconic (Germantown, N.Y.). All mice entered the studies between 7 and 12 weeks of age.

Cell Lines and tissue culture: A20 is a murine B-cell lymphoma cell line originally derived from a BALB/cAnN mouse (American Type Culture Collection, Manassas, Va.). The cells were passaged in vivo, expanded and frozen in aliquots. Single aliquots were thawed as needed for tumor challenge experiments. Mouse BALB/c-3T3 fibroblast were obtained from ATCC and cultured in DMEM medium (Mediatech, Herndon, Va.) supplemented with 100 g/mL penicillin, 100 μg/mL streptomycin, 2 mM glutamine (all from Gibco, Grand Island, N.Y.) and 10% fetal calf serum (HyClone, Logan, Utah). Cells were routinely tested for mycoplasma and found to be negative.

EXAMPLE 1

Plasmid Construction:

Murine CD20 cDNA was obtained by RT-PCR from C57/B6 mouse spleen and from A20 cells. The human counterpart was isolated from normal donor PBMC. Briefly, total RNA was extracted with Trizol reagent (InVitrogen, Carlsbad, Calif.) from 107 cells. The cDNA was synthesized using oligo dT primers and the DNAcycle kit (InVitrogen) as per the kit instructions. CD20 specific primers modified with appropriate restriction sites at the 5' end (in both cases BamHI in the downstream primer and XbaI in the upstream primer) were as follows (all primers were synthesized by Operon, Alameda, Calif.): for the human cDNA the 5' primer had the sequence 5'ATGGATCCTGGA GGA AAT GCT GAG AG3' (Seq. ID No. 1) and the 3' primer 5'GGT CTA GAT GGT GCG TAT GTG CAG AG3' (Seq. ID No. 2) and the resulting product measured 1158 bp and included 118 bp of 5'UTR, 894 bp of ORF and 130 bp of 3'UTR. The sequence of the 5' and 3' mouse primers were 5'AAGGATCCA GTA CAC TGT AGC TAT CTT CAA GTA C3' ((Seq. ID No. 3) and 5'CC TCTAGAA GAG TTT MG GAG CGA TCT C3' (Seq. ID No. 4), respectively. The resulting PCR product measured 1008 bp with 127 bp of 5' UTR, 876 bp of ORF and 5 bp of 3'UTR. PCR were performed for 35 cycles with the following conditions: 95° C. for 3 minutes, followed by 35 cycles of 95° C. for 30 seconds, 56° C. for 30 seconds and 68° C. for 1 minute and 30 seconds, followed by 7 minutes at 68° C. The PCR products were digested with BamHI and XbaI and subcloned into the mammalian expression vector pCR3 (InVitrogen) to create the plasmids pCR3-hCD20 and pCR3-mCD20 (FIGS. 1*a* and 1*b*)(Seq. ID Nos. 5 and 6). The inserts were sequenced and compared to the mouse and human CD20 sequence found in the database. The mouse sequence was identical to the published sequence, while the human sequence had point mutations at position 117 of the ORF (C to T), at position 301 (T to C) and at position 324 (T to C), all of which were silent and likely represent normal polymorphism.

EXAMPLE 2

Figure 1C:
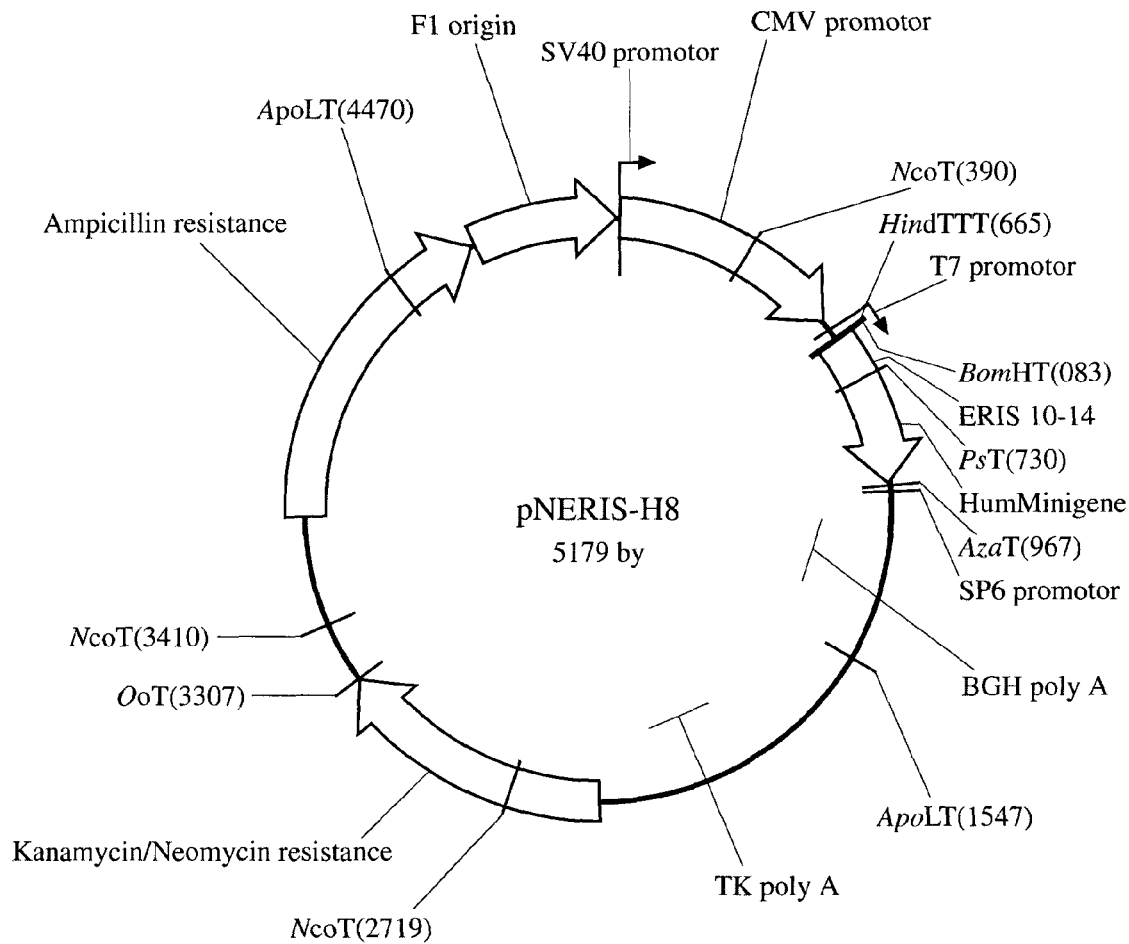
Figure 1D:
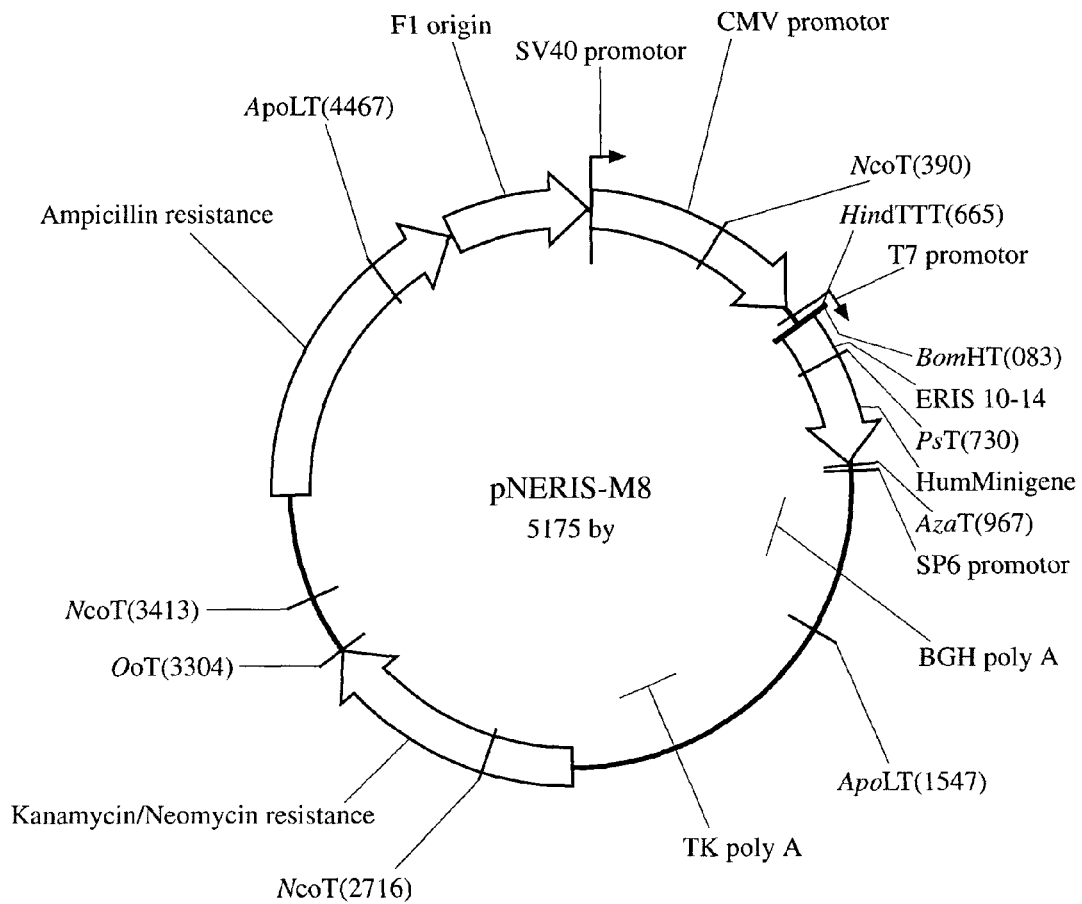
Figure 2A:
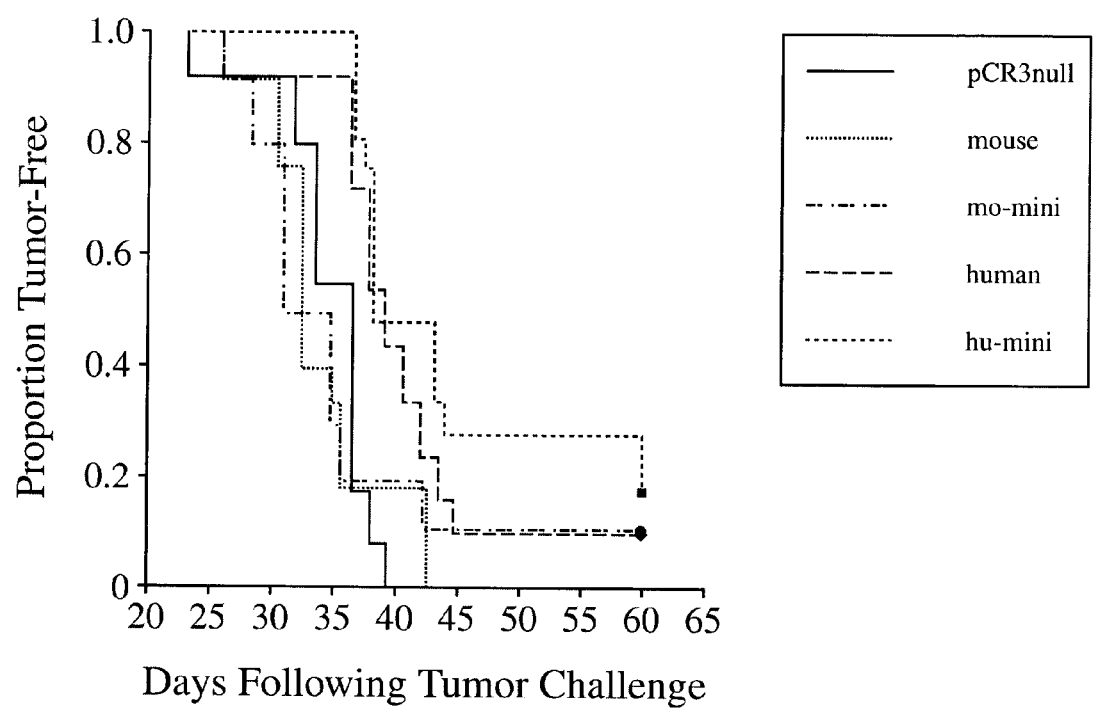
FIGS. 2a-d show Kaplan-Meier survival curves of studies on CD20 genetic immunization.
Figure 2B:
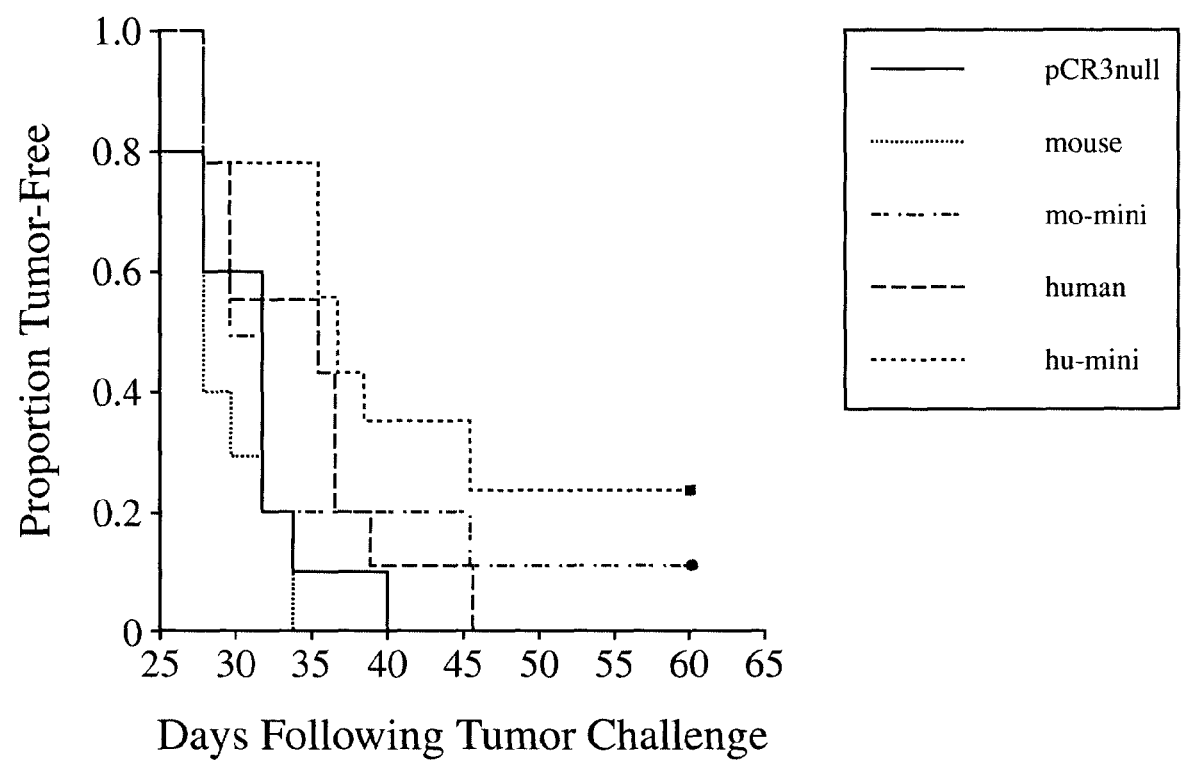
Figure 2C:
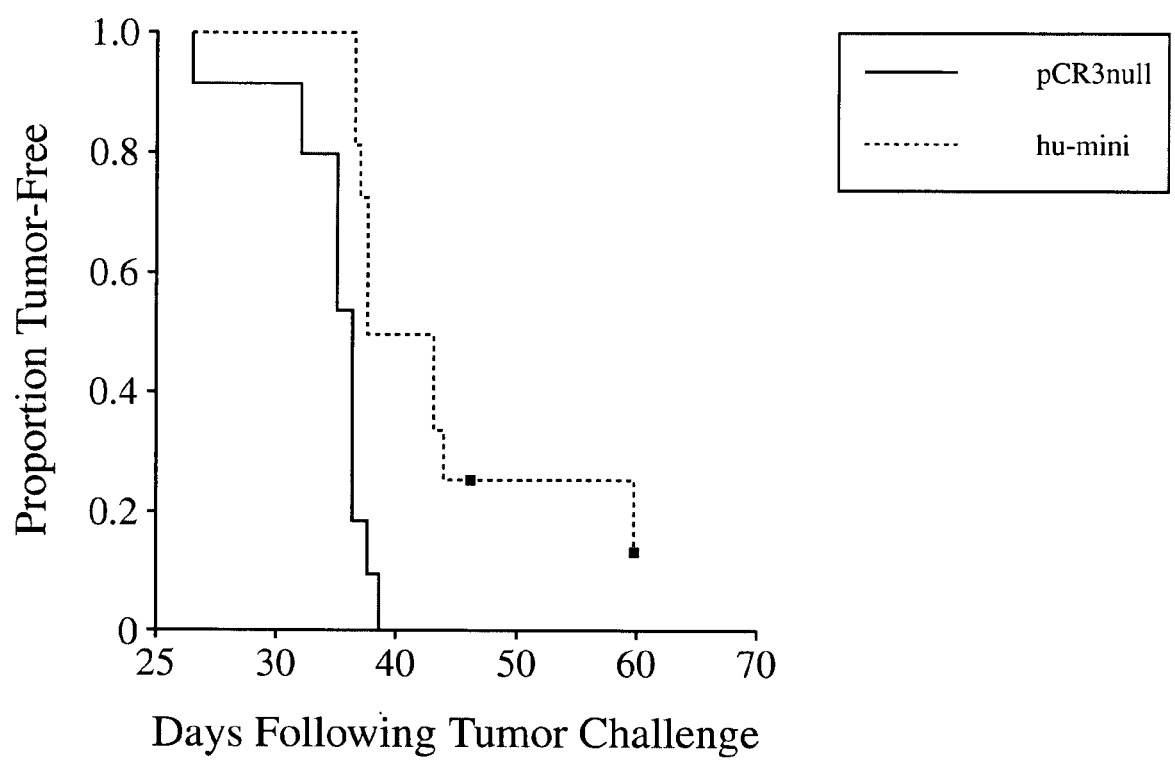
Figure 2D:
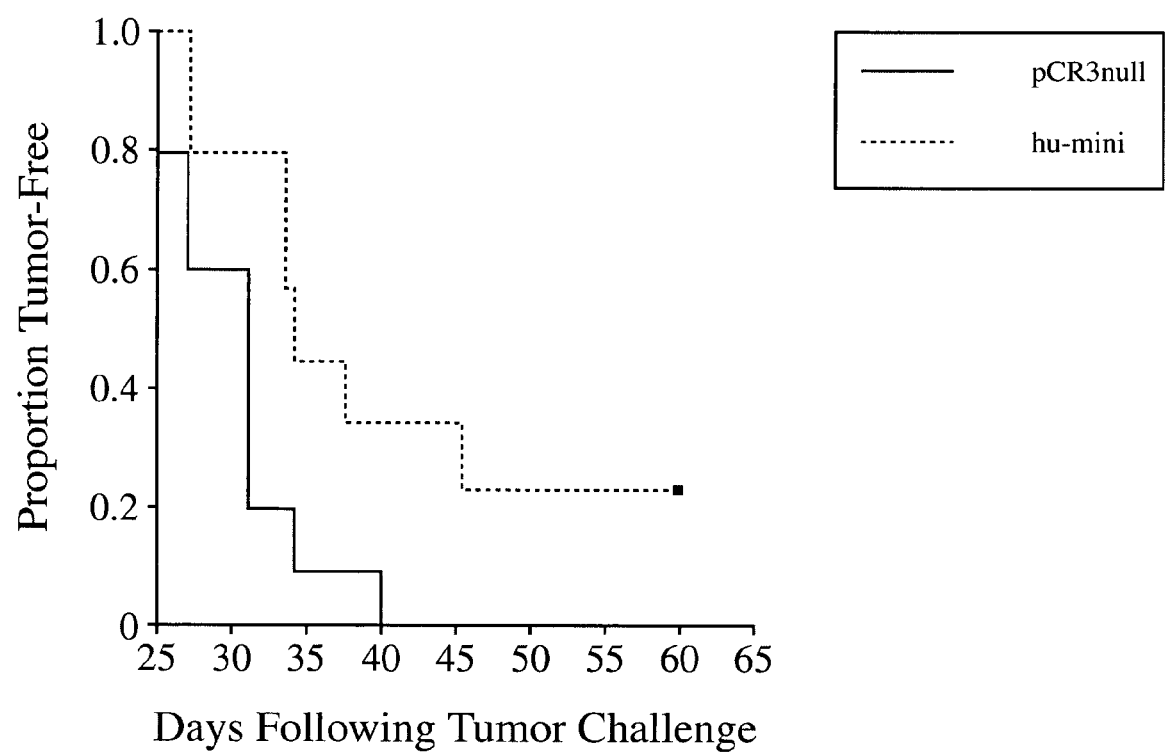

For the construction of the minigenes, the inserts coding for the extracellular domain of CD20 were cloned by PCR into the plasmid pNERIS, in which the minigenes are expressed at the COOH-terminal of an endoplasmic reticulum (ER) insertion sequence derived from the adenovirus E3/19K glycoprotein, driven by the CMV promoter. The following primers were designed: the human downstream primer 5'CTA GCTGCAGTG TGC AGC GCC TCCCATTTTTTAAAAATGGAGAGTC3' (Seq. ID No. 7) (PstI site underlined, hCD20 sequence double underlined), and upstream primer 5'TGCTCGAGT CA ACAGTATTGGGTAGATGGGGAG3' (Seq. ID No. 8)(XhoI site underlined, hCD20 sequence double underlined). The resulting product encodes the entire extracellular domain: KISHFLKMESLNFIR AHTPYINIYNCEPANPSEKNSP-STQYCYS (44 aa, (Seq. ID No. 9)) under the regulation of the CMV promoter. The downstream primer 5'CTA G CTGCA GTG TGC AGC GCC TCTCATTTTTTAAAAATGAGAAGAC3' (Seq. ID No. 10) (PstI site underlined, hCD20 sequence double underlined), and the upstream primer 5'TGCTCGAGT CA ACAGTACTGTGTAGATGGGGAG3' (Seq. ID No.11) (XhoI site underlined, hCD20 sequence double underlined) were used to amplify the mouse extracellular domain with the sequence SHFLKMRRLELIQTSKPYVDIYDC EPSNS-SEKNSPSTQYC (Seq. ID No.12). The PCR products were digested with PstI and XhoI and subcloned into the pNERIS vector to create pNERIS-H8 and pNERIS-M8, respectively (FIGS. 1c and 1d). The plasmid were sequenced for accuracy (Seq. ID Nos. 13 and 14).

EXAMPLE 3

Transfections: BALB/c-3T3 cells were grown to 50-80% confluency. Cells were transfected using the Lipofectamine reagent (InVitrogen) and 1 g each of the plasmids pCR3, pCR3-hCD20, pCR3-mCD20, pNERIS-H8 and pNERIS-M8, as per the manufacturer's instructions. Cell were selected 48 hours after transfection with 1 mg/mL G418 (Gibco). Expression of the transfected DNA was tested by RT-PCR, using the same CD20-specific primers described in the previous section.

EXAMPLE 4

Gene gun immunization: DNA immunization was performed as previously described (Clinical Cancer Research 3:2191). Briefly, 100 µg of DNA from the plasmids described earlier was mixed with 50 mg of 0.95-2.6 µm diameter gold particles in the presence of 0.05 µM spermidine. CaCl2 to a final concentration of 400 mM was added drop wise and the DNA allowed to precipitate onto the gold particles for 10 minutes. The beads were then washed a minimum of three times with 100% ethanol and finally resuspended in 7.2 mL 100% ethanol. This solution was instilled into 50 cm-long plastic Tefzel tubing, the ethanol was gently removed by aspiration and the gold particles were dried with a flow of nitrogen gas at 400 ml/min. The tube was then cut into 0.5 inches bullets. The gold-DNA complexes were injected into the shaved and depilated skin of anesthetized mice using a helium-driven gene gun (Powderject, Inc., Madison, Wis.). Four injections at 400 pounds/inch2 were delivered to each mouse, one per abdominal quadrant, for a total of 4 µg of DNA per mouse. Mice were immunized in this fashion weekly, for a total of five weeks for tumor challenge experiments and for a total of three weeks for ELISPOT assays.

EXAMPLE 5

Tumor challenge and follow-up: Five days following the last of five immunizations, each mouse received 5×104 A20 cells by tail vein injection. The mice were housed in a tail vein illuminator device (Braintree Scientific, Braintree, Mass.) and given the cells resuspended in 200 µl of PBS. Two weeks after the tumor challenge, a baseline weight was taken for each mouse. Generally, symptoms of tumor take included the development of ascites, and consequently weight gain, and palpable abdominal masses arising from the liver and/or spleen. A few mice developed hind legs paralysis. Daily weights were recorded beginning at the third week after tumor challenge. Mice were sacrificed when overtly sick or when they gained 3 g of body weight.

EXAMPLE 6

ELISPOT assays: Groups of five mice were immunized weekly×3. Five to 7 days after the last immunization, mice were sacrificed and the inguinal lymph nodes were isolated and pooled. A single cell suspension was obtained by nylon mesh filtering the disrupted lymph nodes. CD8+ T-cells were isolated by positive selection adding 20 µl of anti mouse CD8 immuno magnetic beads. The cell/beads suspension was run over MACS columns (Miltenyi Biotec Inc., Auburn, Calif.) and washed with MACS buffer (PBS with 0.5% BSA). Cells were eluted with 4 mL of MACS buffer, washed and resuspended in fresh medium. Fifty thousands CD8+T-cells were plated on each well in a 96-well plate coated overnight with 5 pg/ml anti-IFN antibody (Mabtech, Cincinnati, Ohio) in PBS. The cells were incubated at 37 C for 1 hour before overlaying 5×103 3T3 transfectants to each well. Each transfectant cell line was plated in triplicate. Cells were again incubated at 37 C for 20 hours. The next day the cells were washed with PBS/0.05% Tween (PBST) six times. Biotinylated anti-IFN antibody (Mabtech) diluted to 1 µg/mL in PBS/0.5% bovine serum albumin was added to the wells and incubated at 37 C for 2 hours. Plates were washed six times with PBST. Spots were developed with ABC reagent (Vectors Laboratories, Burlington, Calif.) for 30 minutes at room temperature. The reagent was removed with 6 washes with PBS and the spot developed with AEC in 0.5% dimethyl formamide. After 4 minutes the plates were washed with tap water and let air-dry. The plates were read with a Zeiss.

EXAMPLE 7

Production of recombinant mouse CD20 (recCD20) fusion protein: the baculovirus expression system was used to produce a partially purified recCD20 protein for use as a xenoexpressed CD20 antigen. The mouse cDNA was amplified by PCR from pCR3-mCD20 using the same downstream primer described in the plasmid construct section, containing a BamHI site at the 5' end, and the following upstream primer 5'CGGAATTCA GAGTTTAAGGAGCGATCTC3', (SEQ ID NO: 15) containing an EcoRI (underlined, CD20 sequence double underlined). All reagents for the insect expression system were purchased from InVitrogen. The PCR product was digested with BamHI and EcoRI and subcloned into pBlueBacHis2 (b), a vector that expresses CD20 with a 6×His region and a Xpress epitope fused at the N-terminus, under the control of the polyhedrin promoter. The plasmid was transfected into Sf9 cells using the CellFECTIN reagent together with linearized Bac-n-Blue viral DNA following the manufacturer instructions. The final result is recombinant virus with a functional lacZ gene for plaques screening and purification by plaque assay. Two positive recombinant plaques were isolated and propagated. High titer viral stock was prepared from one of the two clones (named B9). The infected cells lysate and the supernatant were tested at several time points by western blot analysis, using the anti-Xpress monoclonal antibody. The expected size of the fusion protein was around 40 kDa.

EXAMPLE 8

Immunoprecipitation and Western blot: After five immunizations, serum was collected from each mouse by eye bleed and preserved at −20 C until needed. Five μL of serum were incubated with 10 μL of recombinant mCD20 overnight at 4 C. All samples were also prepared in the absence of recCD20 as a negative control for the secondary antibody. Ten μL of agarose beads-anti mouse IgG (Sigma., St. Louis, Mo.) were added to the mixture and incubated for 1 hour at 4 C. Beads were washed 5 times with 10 mM Tris-HCl, pH 7.5, 150 mM NaCl, 5 mM EDTA and 1% NP-40 (TNEN), five times with 1/10 strength TNEN and finally five times with distilled water. Proteins were analyzed by 4-20% gradient SDS-polyacrylamide gel electrophoresis under reducing conditions and transferred to Immobilon membrane (Millipore, Bedford, Mass.). The membranes were blocked overnight with 5% non-fat dry milk in TBS-0.05%Tween (TBST), washed with TBST then probed with anti-Xpress antibody diluted 1:5000 in TBST/3%BSA. After three more washes with TBST, the membranes were incubated with HRP-labeled anti mouse IgG (Sigma) diluted at 1:10,000. The membranes were washed again with TBST then developed with ECL reagent (Amersham Biosciences, Piscataway, N.J.) according to the manufacturer's instructions.

```
Sequence of PCR3-mCD20 (Seq. ID No. 6):
gcgcgcgttgacattgattattgactagttattaatagtaatcaattacggggtcattagttcatagcccatatatggag ttccgcgttacataacttacggtaaatggcccgcctggctgaccgcccaacgaccccgcccattgacgtcaataatgac gtatgttcccatagtaacgccaatagggactttccattgacgtcaatgggtggactatttacggtaaactycccacttgg cagtacatcaagtgtatcatatgccaagtacgccccctattgacgtcaatgacggtaaatggcccgcctggcattatgcc cagtacatgaccttatgggactttcctacttggcagtacatctacgtattagtcatcgctattaccatggtgatgcggtt ttggcagtacatcaatgggcgtggatagcggtttgactcacggggatttccaagtctccacccattgacgtcaatggga gtttgttttggcaccaaaatcaacgggactttccaaaatgtcgtaacaactccgccccattgacgcaaatgggcggtagg cgtgtacggtggyaggtctatataagcagagctctctggctaactagagaacccactgcttactggcttatcyaaattaa tacgactcactatagggagacccaagcttggtaccgagctcggatccagtacactgtagctatcttcaagtacttgagat agaagaggccaactgatctcagctgtgagtggctaatttggcccttaagccttgyagccttggagccttggagacccagg cgtttgaaaactcaatgagtggaccttt cccagcagagcctacaaaaggt ccctcgccatgcaacctgctccaaaagtg aacctcaaaaggacatcttcactggtgggcccacacaaagcttcttcatgagggaatcaaaggctttgggggctgtcca aatcatgaatgcctcttccatattaccctgggggg actgctgatgatccccacaggggtcttcgcacccatctgtttga gtgtatggtaccctctctggggaggcattatgtacattatttcaggatcactcctggcagctgcagcagaaaaaacctcc aggaagagtttggtcaaagcaaaagtgataatgagctctctaagcctctttgctgccatttctgyataattctttcaat catggacatacttaacatgacactttctcattttttaaaaatgagaagactggagcttattcaaacttccaagccgtatg ttgatatctacgactgtgaaccatctaattcctcagagaaaaactcccatctacacaytactgtaacagcattcagtct gtgttcttgggcattctgtcggcgatgctgatctctgccttcttccagaaacttgtgacagctggtattgtggagaatga gtggaaaagaatgtgtaccagatccaaatctaatgtggttctgctgtcagctygagaaaaaaatgagcagacgattaaaa tgaaagaagaaatcattgagctaagtggagtatcttcccaaccaaagaatgaagaggaaattgaaattattccagtgcag gaggaagaagaagaagaagcagaaataaattttccagcacctccccaagagcaggaatccttgccagtggaaaatgagat cgctccttaaactcttctagagggccctattctatagtgtcacctaaatgctagagctcgctgatcagcctcgactgtgc cttctagttgccagccatctgttgtttgcccctcccccgtgccttccttgaccctggaaggtgccactccactgtccttt tcctaataaaatgaggaaattgcatcgcattgtctgagtaggtgtcattctattctgggggtggggtgggcaggacag caaggggaggattgggaagacaatagcaggcatgctggggatgcggtgggctctatggcttctgaggcggaaagaacca gtggcggtaatacggttatccacagaatcaggggataacgcaggaaagaacatgtgagcaaaaggccagcaaaaggccag gaaccgtaaaaaggccgcgttgctggcgttttccataggctccgcccccctgacgagcatcacaaaaatcgacgctcaa gtcagaggtggcgaaacccgacaggactataaagataccagycgtttccccctggaagctccctcgtgcgctctcctgtt ccgaccctgccgcttaccggatacctgtccgcctttctcccttcgggaagcgtggcgctttctcatagctcacgctgtag gtatctcagttcggtgtaggtcgttcgctccaagctgggctgtgtgcacgaaccccccgttcagcccgaccgctgcgcct tatccggtaactatcgtcttgagtccaacccggtaagacacgacttatcgccactggcagcagccactggtaacaggatt
```

-continued

```
agcagagcgaggtatgtaggcggtgctacagagttcttgaagtggtggcctaactacggctacactagaaggacagtatt
tggtatctgcgctctgctgaagccagttaccttcggaaaaagagttggtagctcttgatccggcaaacaaaccaccgctg
gtagcggtggttttttttgtttgcaagcagcagattacgcgcagaaaaaaaggatctcaagaagatcctttgatcttttct
acggggtctgacgctcagtggaacgaaaactcacgttaagggattttggtcatgagattatcaaaaaggatcttcaccta
gatccttttaaattaaaaatgaagttttaaatcaatctaaagtatatatgagtaacctgaggctatggcagggcctgccg
ccccgacgttggctgcgagccctgggccttcacccgaacttgggggggtggggtggggaaaaggaagaaacgcgggcgtat
tggcccaatggggtctcggtggggtatcgacagagtgccagccctgggaccgaaccccgcgtttatgaacaaacgaccc
aacaccgtgcgttttattctgtctttttattgccgtcatagcgcgggttccttccgttattgtctccttccgtgtttcag
ttagcctcccctagggtgggcgaagaactccagcatgagatccccgcgctggaggatcatccagccggcgtcccggaaa
acgattccgaagcccaacctttcatagaaggcggcggtggaatcgaaatctcgtgatggcaggttgggcgtcgcttggtc
ggtcatttcgaaccccagagtcccgctcagaagaactcgtcaagaaggcgatagaaggcgatgcgctgcgaatcgggagc
ggcgataccgtaaagcacgaggaagcggtcagcccattcgccgccaagctcttcagcaatatcacgggtagccaacgcta
tgtcctgatagcggtccgccacacccagccggccacagtcgatgaatccagaaaagcggccattttccaccatgatattc
ggcaagcaggcatcgccatgggtcacgacgagatcctcgccgtcgggcatgctcgccttgagcctggcgaacagttcggc
tggcgcgagccctgatgctcttgatcatcctgatcgacaagaccggcttccatccgagtacgtgctcgctcgatgcgat
gtttcgcttggtggtcgaatgggcaggtagccggatcaagcgtatgcagccgccgcattgcatcagccatgatggatact
ttctcggcaggagcaaggtgagatgacaggagatccyccccggcacttcgcccaatagcagccaytccctcccgcttc
agtgacaacgtcgagcacagctgcgcaaggaacgcccgtcgtggccagccacgatagccgcgctgcctcgtcttgcagtt
cattcagggcaccggacaggtcggtcttgacaaaaagaaccgggcgcccctgcgctgacagccgyaacacggcggcatca
gagcagccgattgtctgttgtgcccagtcatagccgaatagcctctccacccaagcggccggagaacctgcgtgcaatcc
atcttgttcaatcatgcgaaacgatcctcatcctgtctcttgatcgatctttgcaaaagcctaggcctccaaaaaagcct
cctcactacttctggaatagctcagaggccgaggcggcctcggcctctgcataaataaaaaaaattagtcagccatgggg
cggagaatgggcggaactgggcggagttaggggcgggatgggcggagttaggggcgggactatggttgctgactaattga
gatgcatyctttgcatacttctgcctgctggggagcctggggactttccacacctggttgctgactaattgagatgcatg
ctttgcatacttctgcctgctggggagcctggggactttccacaccctaactgacacacattccacagctggttctttcc
gcctcaggactcttccttttcaataaatcaatctaaagtatatatgagtaaacttggtctgacagttaccaatgcttaa
tcagtgaggcacctatctcagcgatctgtctatttcgttcatccatagttgcctgactccccgtcgtgtagataactacg
atacgggagggcttaccatctggccccagtgctgcaatgataccgcgagacccacgctcaccggctccagatttatcagc
aataaaccagccayccggaagggccgagcgcagaagtggtcctgcaactttatccgcctccatccagtctattaattgtt
gccgggaagctagagtaagtagttcgccagttaatagtttgcgcaacgttgttgccattgctacaggcatcgtggtgtca
cgctcgtcgtttggtatggcttcattcagctccggttcccaacgatcaaggcgagttacatgatcccccatgttgtgcaa
aaaagcggttagctccttcggtcctccgatcgttgtcagaagtaagttggccgcagtgttatcactcatggttatggcag
cactgcataattctcttactgtcatgccatccgtaagatgcttttctgtgactggtgagtactcaaccaagtcattctga
gaatagtgtatgcggcgaccgagttgctcttgcccggcgtcaatacgggataataccgcgccacatagcagaactttaaa
agtgctcatcattggaaaacgttcttcggggcgaaaactctcaaggatcttaccgctgttgagatccagttcgatgtaac
ccactcgtgcacccaactgatcttcagcatcttttactttcaccagcgtttctgggtgagcaaaaacaggaaggcaaaat
gccgcaaaaaagggaataagggcgacacggaaatgttgaatactcatactcttcctttttcaatattattgaagcattta
tcagggttattgtctcatgagcggatacatatttgaatgtatttagaaaaataaacaataggggttccgcgcacatttc
cccgaaaagtgccacctgacgcgccctgtagcggcgcattaagcgcggcgggtgtggtggttacgcgcagcgtgaccgct
acacttgccagcgccctagcgcccgctcctttcgctttcttcccttcctttctcgccacgttcgccggctttccccgtca
agctctaaatcggggctccctttagggttccgatttagtgctttacggcacctcgaccccaaaaaacttgattagggtg
```

-continued atggttcacgtagtgggccatcgccctgatagacggttttcgccctttgacgttggagtccacgttctttaatagtgga ctcttgttccaaactggaacaacactcaaccctatctcggtctattcttttgatttataagggattttgccgatttcggc ctattggttaaaaaatgagctgatttaacaaaaatttaacgcgaattttaacaaaatattaacgcttacaatttac Sequence of pCR3-hCD20 (Seq ID No. 5):
gcgcgcgttgacattgattattgactagttattaatagtaatcaattacggggtcattagttcatagcccatatatggag ttccgcgttacataacttacggtaaatggcccgcctggctgaccgcccaacgacccccgcccattgacgtcaataatgac gtatgttcccatagtaacgccaataggactttccattgacgtcaatgggtggactatttacggtaaactgcccacttgg cagtacatcaagtgtatcatatgccaagtacgccccctattgacgtcaatgacggtaaatggcccgcctggcattatgcc cagtacatgaccttatgggactttcctacttggcagtacatctacgtattagtcatcgctattaccatggtgatgcggtt ttggcagtacatcaatgggcgtggatagcggtttgactcacggggatttccaagtctccaccccattgacgtcaatggga gtttgttttggcaccaaaatcaacgggactttccaaaatgtcgtaacaactccgccccattgacgcaaatgggcggtagg cgtgtacggtgggaggtctatataagcagagctctctggctaactagagaacccactgcttactggcttatcgaaattaa tacgactcactatagggagacccaagcttggtaccgagctcggatccaagcattcagatgcatgacacaaggtaagactg ccaaaaatcttgttcttgctctcctcattttgttatttgttttattttaggagttttgagagcaaaatgacaacaccca gaaattcagtaaatgggactttcccggcagagccaatgaaaggccctattgctatgcaatctggtccaaaaccactcttc aggaggatgtcttcactggtgggccccacgcaaagcttcttcatgagggaatctaagactttgggggctgtccagattat gaatgggctcttccacattgccctggggggtcttctgatgatcccagcagggatctatgcacccatctgtgtgactgtgt ggtaccctctctggggaggcattatgtatattatttccggatcactcttggcagcaacggagaaaaactctaggaagtgt ttggtcaaaggaaaaatgataatgaattcattgagcctctttgctgccatttctggaatgattctttcaatcatggacat acttaatattaaaatttcccatttttaaaaatggagagtctgaattttattagagctcacacaccatatattaacatat acaactgtgaaccagctaatccctctgagaaaaactccccatctacccaatactgttacagcatacaatctctgttcttg ggcattttgtcagtgatgctgatctttgccttcttccaggaacttgtaatagctggcatcgttgagaatgaatgaaaag aacgtgctccagacccaaatctaacatagttctcctgtcagcagaagaaaaaaagaacagactattgaaataaaagaag aagtggttgggctaactgaaacatcttcccaaccaaagaatgaagaagacattgaaattattccaatccaagaagaggaa gaagaagaaacagagacgaactttccagaaccctcccaagatcaggaatcctcaccaatagaaaatgacagctctcctta agtgatttcttctgttttctgtttccttttttaaacattagtgttcatagcttccaagagacaggtctagagggccctat tctatagtgtcacctaaatgctagagctcgctyatcagcctcgactgtgccttctagttgccagccatctgttgtttgcc cctcccccgtgccttccttgaccctggaaggtgccactcccactgtcctttcctaataaaatgaggaaattgcatcgcat tgtctgagtaggtgtcattctattctgggggtggggtggggcaggacagcaaggggaggattgggaagacaatagcag gcatgctggggatgcggtgggctctatggcttctgaggcggaaagaaccagtggcggtaatacggttatccacagaatca ggggataacgcaggaaagaacatgtgagcaaaaggccagcaaaaggccaggaaccgtaaaaaggccgcgttgctggcgtt tttccataggctccgcccccctgacgagcatcacaaaaatcgacgctcaagtcagaggtggcgaaacccgacaggactat aaagataccaggcgtttccccctggaagctccctcgtgcgctctcctgttccgaccctgccgcttaccggatacctgtcc gcctttctcccttcgggaagcgtggcgctttctcatagctcacgctgtaggtatctcagttcggtgtaggtcgttcgctc caagctgggctgtgtgcacgaaccccccgttcagcccgaccgctgcgccttatccggtaactatcgtcttgagtccaacc cggtaagacacgacttatcgccactggcagcagccactggtaacaggattagcagagcgaggtatgtaggcggtgctaca gagttcttgaagtggtggcctaactacggctacactagaaggacagtatttggtatctgcgctctgctgaagccagttac cttcggaaaaagagttggtagctcttgatccggcaaacaaaccaccgctggtagcggtggtttttttgtttgcaagcagc agattacgcgcagaaaaaaaggatctcaagaagatcctttgatcttttctacggggtctgacgctcagtggaacgaaaac tcacgttaagggattttggtcatgagattatcaaaaaggatcttcacctagatccttttaaattaaaaatgaagttttaa atcaatctaaagtatatatgagtaacctgaggctatggcagggcctgccgccccgacgttggctgcgagccctgggcctt -continued

```
cacccgaacttggggggtgggtggggaaaaggaagaaacgcgggcgtattggccccaatggggtctcggtggggtatcg acagagtgccagccctgggaccgaaccccgcgtttatgaacaaacgacccaacaccgtgcgttttattctgtctttttat tgccgtcatagcgcgggttccttccggtattgtctccttccgtgtttcagttagcctcccccctagggtgggcgaagaact ccagcatgagatccccgcgctggaggatcatccagccggcgtcccggaaaacgattccgaagcccaacctttcatagaag gcggcggtggaatcgaaatctcgtgatggcaggttgggcgtcgcttggtcggtcatttcgaaccccagagtcccgctcag aagaactcgtcaagaaggcgatagaaggcgatgcgctgcgaatcgggagcggcgataccgtaaagcacgaggaagcggtc agcccattcgccgccaagctcttcagcaatatcacgggtagccaacgctatgtcctgatagcggtccgccacacccagcc ggccacagtcgatgaatccagaaaagcggccattttccaccatgatattcggcaagcaggcatcgccatgggtcacgacg agatcctcgccgtcgggcatgctcgccttgagcctggcgaacagttcggctggcgcgagcccctgatgctcttgatcatc ctgatcgacaagaccggcttccatccgagtacgtgctcgctcgatgcgatgtttcgcttggtggtcgaatgggcaggtag ccggatcaagcgtatgcagccgccgcattgcatcagccatgatggatactttctcggcaggagcaaggtgagatgacagg agatcatgcccggcacttcgcccaatagcagccagtcccttcccgcttcagtgacaacgtcgagcacagctgcgcaagg aacgcccgtcgtggccagccacgatagccgcgctgcctcgtcttgcagttcattcagggcaccggacaggtcggtcttga caaaagaaccgggcgccctgcgctgacagccggaacacggcggcatcagagcagccgattgtctgttgtgcccagtca tagccgaatagcctctccacccaagaggccggagaacctgcgtgcaatccatcttgttcaatcatgcgaaacgatcctca tcctgtctcttgatcgatctttgcaaaagcctaggcctccaaaaaagcctcctcactacttctggaatagctcagaggcc gaggcggcctcggcctctgcataaataaaaaaaattagtcagccatggggcggagaatgggcggaactgggcggagttag gggcgggatgggcggayttaggggcgggactatggttgctgactaattgagatgcatgctttgcatacttctgcctgctg gggagcctygggactttccacacctggttgctgactaattgagatgcatgctttgcatacttctgcctgctggggagcct ggggactttccacaccctaactgacacacattccacagctggttctttccgcctcaggactcttccttttttcaataaatc aatctaaagtatatatgagtaaacttggtctgacagttaccaatgcttaatcagtgaggcacctatctcagcgatctgtc tatttcgttcatccatagttgcctgactccccgtcgtgtagataactacgatacgggagggcttaccatctggccccagt gctgcaatgataccgcgagacccacgctcaccggctccagatttatcagcaataaaccagccagccggaagggccgagcg cagaagtggtcctgcaactttatccgcctccatccagtctattaattgttgccgggaagctagagtaagtagttcgccag ttaatagtttgcgcaacgttgttgccattgctacaggcatcgtggtgtcacgctcgtcgtttggtatggcttcattcagc tccggttcccaacgatcaaggcgagttacatgatcccccatgttgtgcaaaaaagcggttagctccttcggtcctccgat cgttgtcagaagtaagttggccgcagtgttatcactcatggttatggcagcactgcataattctcttactgtcatgccat ccgtaagatgcttttctgtgactggtgagtactcaaccaagtcattctgagaatagtgtatgcggcgaccgagttgctct tgcccggcgtcaatacgggataataccgcgccacatagcagaactttaaaagtgctcatcattggaaaacgttcttcggg gcgaaaactctcaaggatcttaccgctgttgagatccagttcgatgtaacccactcgtgcacccaactgatcttcagcat cttttactttcaccagcgtttctgggtgagcaaaaacaggaaggcaaaatgccgcaaaaaagggaataagggcgacacgg aaatgttgaatactcatactcttcctttttcaatattattgaagcatttatcagggttattgtctcatgagcggatacat atttgaatgtatttagaaaaataaacaataggggttccgcgcacatttccccgaaaagtgccacctgacgcgccctgta gcggcgcattaagcgcggcgggtgtggtggttacgcgcagcgtgaccgctacacttgccagcycctagcgcccgctcct ttcgctttcttcccttcctttctcgccacgttcgccggctttccccgtcaagctctaaatcggggctccctttagggtt ccgatttagtgctttacggcacctcgaccccaaaaaacttgattagggtgatggttcacgtagtgggccatcgccctgat agacggttttcgccctttgacgttggagtccacgttctttaatagtggactcttgttccaaactggaacaacactcaac cctatctcggtctattcttttgatttataagggattttgccgatttcggcctattggttaaaaatgagctgatttaaca aaaatttaacgcgaattttaacaaaatattaacgcttacaatttac
```

-continued

Sequence of pNERIS-M8 (Seq ID No. 14):
gcgcgcgttgacattgattattgactagttattaatagtaatcaattacggggtcattagttcatagcccatatatggag ttccgcgttacataacttacggtaaatggcccgcctggctgaccgcccaacgaccccgcccattgacgtcaataatgac gtatgttcccatagtaacgccaataggggactttccattgacgtcaatgggtggactatttacggtaaactgcccacttgg cagtacatcaagtgtatcatatgccaagtacgccccctattgacgtcaatgacggtaaatggcccgcctggcattatgcc cagtacatgaccttatgggactttcctacttggcagtacatctacgtattagtcatcgctattaccatggtgatgcggtt ttggcagtacatcaatgggcgtggatagcggtttgactcacggggatttccaagtctccaccccattgacgtcaatggga gtttgttttggcaccaaaatcaacgggactttccaaaatgtcgtaacaactccgccccattgacgcaaatgggcggtagg cgtgtacggtgggaggtctatataagcagagctctctggctaactagagaacccactgcttactggcttatcgaaattaa tacgactcactatagggagacccaagcttggtaccgagctcggatccaccatgagatacatgatcctgggcctgctggcc ctggctgcagtgtgcagcgcctctcattttttaaaaatgagaagactggagcttattcaaacttccaagccgtatgttga tatctacgactgtgaaccatctaattcctcagagaaaaactccccatctacacagtactgttctcgagcatgcatctaga gggcccattctatagtgtcacctaaatgctagagctcgctgatcagcctcgactgtgccttctagttgccagccatctg ttgtttgcccctcccccgtgccttccttgaccctggaaggtgccactcccactgtcctttcctaataaaatgaggaaatt gcatcgcattgtctgagtaggtgtcattctattctgggggtggggtggggcaggacagcaaggggggaggattgggaaga caatagcaggcatgctggggatgcggtgggctctatggcttctgaggcggaaagaaccagtggcggtaatacggttatcc acagaatcaggggataacgcaggaaagaacatgtgagcaaaaggccagcaaaaggccaggaaccgtaaaaaggccgcgtt gctggcgtttttccataggctccgcccccctgacgagcatcacaaaaatcgacgctcaagtcagaggtggcgaaacccga caggactataaagataccaggcgtttccccctggaagctccctcgtgcgctctcctgttccgaccctgccgcttaccgga tacctgtccgcctttctcccttcgggaagcgtggcgctttctcatagctcacgctgtaggtatctcagttcggtgtaggt cgttcgctccaagctgggctgtgtgcacgaaccccccgttcagcccgaccgctgcgccttatccggtaactatcgtcttg agtccaacccggtaagacacgacttatcgccactggcagcagccactggtaacaggattagcagagcgaggtatgtaggc ggtgctacagagttcttgaagtggtggcctaactacggctacactagaaggacagtatttggtatctgcgctctgctgaa gccagttaccttcggaaaaagagttggtagctcttgatccggcaaacaaaccaccgctggtagcggtggtttttttgttt gcaagcagcagattacgcgcagaaaaaaaggatctcaagaagatcctttgatcttttctacggggtctgacgctcagtgg aacgaaaactcacgttaagggattttggtcatgagattatcaaaaaggatcttcacctagatccttttaaattaaaaatg aagttttaaatcaatctaaagtatatatgagtaaacctgaggctatggcagggcctgccgccccgacgttggctgcgagcc ctgggccttcacccgaacttggggggtggggtggggaaaaggaagaaacgcgggcgtattggccccaatggggtctcggt ggggtatcgacagagtgccagccctgggaccgaaccccgcgtttatgaacaaacgacccaacaccgtgcgttttattctg tcttttattgcgtcatagcgcgggttccttccggtattgtctccttccgtgtttcagttagcctcccccctagggtggg cgaagaactccagcatgagatccccgcgctggaggatcatccagccggcgtcccggaaaacgattccgaagcccaacctt tcatagaaggcggcggtggaatcgaaatctcgtgatggcaggttgggcgtcgcttggtcggtcatttcgaacccagagt cccgctcagaagaactcgtcaagaaggcgatagaaggcgatgcgctgcgaatcgggagcggcgataccgtaaagcacgag gaagcggtcagcccattcgccgccaagctcttcagcaatatcacgggtagccaacgctatgtcctgatagcggtccgcca cacccagccggccacagtcgatgaatccagaaaagcggccattttccaccatgatattcggcaaycagycatcgccatgg gtcacgacgagatcctcgccgtcgggcatgctcgccttgagcctggcgaacayttcggctggcgcgagcccctgatgctc ttgatcatcctgatcgacaagaccggcttccatccgagtacgtgctcgctcgatgcgatgtttcgcttggtygtcgaatg ggcaggtagccggatcaagcgtatgcagccgccgcattgcatcagccatgatggatactttctcggcaggagcaaggtga gatgacaggagatcctgacccggcacttcgcccaatagcagccagtcccttcccgcttcagtgacaacgtcgagcacagc tgcgcaaggaacgcccgtcgtggccagccacyatagccgcgctgcctcgtcttgcagttcattcagggcaccggacaggt cggtcttgacaaaaagaaccgggcgcccctgcgctgacagccggaacacggcggcatcagagcagccgattgtctgttgt -continued

```
gcccagtcatagccgaatagcctctccacccaagcggccggagaacctgcgtgcaatccatcttgttcaatcatgcgaaa
cgatcctcatcctgtctcttgatcgatctttgcaaaagcctaggcctccaaaaaagcctcctcactacttctggaatagc
tcagaggccgaggcggcctcggcctctgcataaataaaaaaaattagtcagccatggggcggagaatyggcggaactggg
cggagttaggggcgggatgggcggagttaggggcgggactatggttgctgactaattgagatgcatgctttgcatacttc
tgcctgctggggagcctggggacttcaacacctggttgctgactaattgagatgcatgctttgcatacttctgcctgct
ggggagcctggggacttccacacccaactgacacacattccacagctggttctttccgcctcaggacccttccttttt
caataaatcaatctaaagtatatatgagtaaacttggtctgacagttaccaatgcttaatcagtgaggcacctatctcag
cgatctgtctatttcgttcatccatagttgcctgactccccgtcgtgtagataactacgatacgggagggcttaccatct
ggccccagtgctgcaatgataccgcgagacccacgctcaccggctccagatttatcagcaataaaccagccagccggaag
ggccgagcgcagaagtggtcctgcaactttatccgcctccatccagtctattaattgttgccgggaagctayagtaagta
gttcgccagttaatagtttgcgcaacgttgttgccattgctacaggcatcgtggtgtcacgctcgtcgtttggtatggct
tcattcagctccggttcccaacgatcaaggcgagttacatgatccccatgttgtgcaaaaaagcggttagctccttcgg
tcctccgatcgttgtcagaagtaagttggccgcagtgttatcactcatggttatggcagcactgcataattctcttactg
tcatgccatccgtaagatgcttttctgtgactggtgagtactcaaccaagtcattctgagaatagtgtatgcggcgaccg
agttgctcttgcccggcgtcaatacgggataataecgcgccacatagcagaactttaaaagtgctcatcattggaaaacg
ttcttcggggcgaaaactctcaaggatcttaccgctgttgagatccagttcgatgtaacccactcgtgcacccaactgat
cttcagcatcttttactttcaccagctgtttctgggtgagcaaaaacaggaaggcaaaatgccgcaaaaagggaataagg
gcgacacggaaatgttgaatactcatactcttccttttcaatattattgaagcatttatcagggttattgtctcatgag
cggatacatatttgaatgtatttagaaaaataaacaaatagggqttccgcgcacatttccccgaaaagtgccacctgacg
cgccctgtagcggcgcattaagcgcggcyggtgtggtggttacgcgcagcgtgaccgctacacttgccagcgccctagcg
cccgctcctttcgctttcttcccttcctttctcgccacgttcgccggctttccccgtcaagctctaaatcggggggctccc
tttagggttccgatttagtgctttacggcacctcgaccccaaaaaacttgattagggtgatggttcacgtagtgggccat
cgccctgatagacggttttcgccctttgacgttggagtccacgttctttaatagtggactcttgttccaaactggaaca
acactcaaccctatctcggtctattcttttgattttataagggattttgccgatttcggcctattggttaaaaatgagct
gatttaacaaaaatttaacgcgaattttaacaaaatattaacgcttacaatttac
```

Sequence of pNERIS-H8 (Seq ID No. 13):

```
gcgcgcgttgacattgattattgactagttattaatagtaatcaattacggggtcattagttcatagcccatatatggag
ttccgcgttacataacttacggtaaatggcccgcctggctgaccgcccaacgaccccccgcccattgacgtcaataatgac
gtatgttcccatagtaacgccaatagggactttccattgacgtcaatgggtggactatttacggtaaactgcccacttgg
cagtacatcaagtgtatcatatgccaagtacgccccctattgacgtcaatgacggtaaatggcccgcctggcattatgcc
cagtacatgaccttatgggactttcctacttggcagtacatctacgtattagtcatcgctattaccatggtgatgcggtt
ttggcagtacatcaatgggcgtggatagcggtttgactcacggggatttccaagtctccaccccattgacgtcaatggga
gtttgttttggcaccaaaatcaacgggactttccaaaatgtcgtaacaactccgccccattgacgcaaatgggcggtagg
cgtgtacggtgggaggtctatataagcagagctctctggctaactagagaacccactgcttactggcttatcgaaattaa
tacgactcactatagggagacccaagcttggtaccgagctcggatccaccatgagatacatgatcctgggcctgctggcc
ctggctgcagtgtgcagcgcctcccattttttaaaaatggagagtctgaattttattagayctcacacaccatatattaa
catatacaactgtgaaccagctaatccctctgagaaaaactccccatctacccaatactgttcatctcgagcatgcatct
agagggccctattctatagtgtcacctaaatgctagagctcgctgatcagcctcgactgtgccttctagttgccagccat
ctgttgtttgcccctcccccgtgccttccttgaccctggaaggtgccactcccactgtcctttcctaataaaatgaggaa
attgcatcgcattgtctgagtaggtgtcattctattctggggggtgggtggggcaggacagcaaggggaggattggga
agacaatagcaggcatgctggggatgcggtgggctctatggcttctgaggcggaaagaaccagtggcggtaatacggtta
```

-continued

```
tccacagaatcaggggataacgcaggaaagaacatgtgagcaaaaggccagcaaaaggccaggaaccgtaaaaaggccgc gttgctggcgttttttccataggctccgcccccctgacgagcatcacaaaaatcgacgctcaagtcagaggtggcgaaacc cgacaggactataaagataccaggcgtttccccctggaagctccctcgtgcgctctcctgttccgaccctgccgcttacc ggatacctgtccgcctttctcccttcgggaagcgtggcgctttctcatagctcacgctgtaggtatctcagttcggtgta ggtcgttcgctccaagctgggctgtgtgcacgaaccccccgttcagcccgaccgctgcgccttatccggtaactatcgtc ttgagtccaacccggtaagacacgacttatcgccactggcagcagccactggtaacaggattagcagagcgaggtatgta ggcggtgctacagagttcttgaagtggtggcctaactacggctacactagaaggacagtatttggtatctgcyctctgct gaagccagttaccttcggaaaaagagttggtagctcttgatccggcaaacaaaccaccgctggtagcggtggtttttttg tttgcaagcagcagattacgcgcagaaaaaaaggatctcaagaagatcctttgatcttttctacggggtctgacgctcag tggaacgaaaactcacgttaagggattttggtcatgagattatcaaaaaggatcttcacctagatccttttaaattaaaa atgaagttttaaatcaatctaaagtatatatgagtaaacctgaggctatggcagggcctgccgcccccgacgttggctgcga gccctgggccttcacccgaacttgggggtgggtgggaaaaggaagaaacgcgggcgtattggccccaatgggtctc ggtggggtatcgacagagtgccagccctgggaccgaaccccgcgtttatgaacaaacgacccaacaccgtgcgttttatt ctgtcttttattgccgtcatagcgcgggttccttccggtattgtctccttccgtgtttcagttagcctccccctagggt gggcgaagaactccagcatgagatccccgcgctggaggatcatccagccggcgtcccggaaaacgattccgaagcccaac cttcatagaaggcggcggtggaatcgaaatctcgtgatggcaggttgggcgtcgcttggtcggtcatttcgaacccag agtcccgctcagaagaactcgtcaagaaggcgatagaaggcgatgcgctgcgaatcgggagcggcgataccgtaaagcac gaggaagcggtcagcccattcgccgccaagctcttcagcaatatcacgggtagccaacgctatgtcctgatagcggtccg ccacacccagccggccacagtcgatgaatccagaaaagcggccattttccaccatgatattcggcaagcaggcatcycca tgggtcacgacgagatcctcgccgtcgggcatgctcgccttgagcctggcgaacagttcggctggcgcgayccctgatg ctcttgatcatcctgatcgacaagaccggcttccatccgagtacgtgctcgctcgatgcgatgtttcgcttggtggtcga atgggcaggtagccggatcaagcgtatgcagccgccgcattgcatcagccatgatggatactttctcggcaggagcaagg tgagatgacaggagatcctgccccggcacttcgcccaatagcagccagtcccttcccgcttcagtgacaacgtcgagcac agctgcgcaaggaacgcccgtcgtggccagccacgatagccgcgctgcctcgtcttgcagttcattcagggcaccggaca ggtcggtcttgacaaaaagaaccgggcgcccctgcgctgacagccggaacaaggcggcatcagagcagccgattgtctgt tgtgcccagtcatagccgaatagcctctccacccaagcggccggagaacctgcgtgcaatccatcttgttcaatcatgcg aaacgatcctcatcctgtctcttgatcgatctttgcaaaagcctaggcctccaaaaaagcctcctcactacttctggaat agctcagaggccgaggcggcctcggcctctgcataaataaaaaaaattagtcagccatggggcggagaatgggcggaact gggcggagttaggggcgggatgggcggagttaggggcgggactatggttgctgactaattgagatgcatgctttgcatac ttctgcctgctggggagcctggggactttccacacctggttgctgactaattgagatgcatgctttgcatacttctgcct gctggggagcctggggactttccacaccctaactgacacacattccacagctggttctttccgcctcaggactcttcctt tttcaataaatcaatctaaagtatatatgagtaaacttggtctgacagttaccaatgcttaatcagtgaggcacctatct cagcgatctgtctatttcgttcatccatagttgcctgactccccgtcgtgtagataactacgatacgggagggcttacca tctggccccagtgctgcaatgataccgcgagacccacgctcaccggctccagatttatcagcaataaaccagccagccgg aagggccgagcgcagaagtggtcctgcaactttatccgcctccatccagtctattaattgttgccgggaagctagagtaa gtagttcgccagttaatagtttcgcgcaacgttgttgccattgctacaggcatcgtggtgtcacgctcgtcgtttggtatg gcttcattcagctccggttcccaacgatcaaggcgagttacatgatccccatgttgtgcaaaaaagcggttagctcctt cggtcctccgatcgttgtcagaagtaagttggccgcagtgttatcactcatggttatggcagcactgcataattctctta ctgtcatgccatccgtaagatgcttttctgtgactggtgagtactcaaccaagtcattctgagaatagtgtatgcggcga ccgagttgctcttgcccggcgtcaatacgggataataccgcgccacatagcagaactttaaaagtgctcatcattggaaa acgttcttcggggcgaaaactctcaaggatcttaccgctgttgagatccagttcgatgtaacccactcgtgcacccaact
```

-continued

```
gatcttcagcatctttactttcaccagcgtttctgggtgagcaaaaacaggaaggcaaaatyccgcaaaaaagggaata agggcgacacggaaatgttgaatactcatactcttccttttcaatattattgaagcatttatcaggttattgtctcat gagcggatacatatttgaatgtatttagaaaaataaacaatagggttccgcgcacatttccccgaaaagtgccacctg acgcgccctgtagcggcgcattaagcgcggcgggtgtggtggttacgcgcagcgtgaccgctacacttgccagcgccta gcgcccgctcctttcgctttcttcccttcctttctcgcgacgttcgccggctttccccgtcaagctctaaatcgggggct ccctttagggttccgatttagtgctttacggcacctcgaccccaaaaaacttgattagggtgatggttcacgtagtgggc catcgccctgatagacggtttttcgccctttgacgttggagtccacgttctttaatagtggactcttgttccaaactgga acaacactcaaccctatctcggtctattctttgatttataagggattttgccgatttcggcctattggttaaaaaatga gctgatttaacaaaaatttaacgcgaattttaacaaaatattaacgcttacaattttac
```

---

We claim:

1. A method for stimulating an immune response to a tissue expressing CD20 in a subject individual of a first species, comprising administering to the subject individual an immunologically-effective amount of xenogeneic or xenoexpressed CD20 antigen.

2. The method according to claim 1, wherein the subject individual of the first species is human.

3. The method of claim 2, wherein the CD20 antigen is a xenogeneic CD20 antigen selected from the group consisting of rodent, dog, cat, cow and sheep CD20 antigen.

4. The method of claim 2, wherein the step of administering is achieved by immunization with a vaccine comprising purified xenogeneic or xenoexpressed CD20 antigen.

5. The method of claim 4, wherein the vaccine also comprises an adjuvant.

6. The method of claim 5, wherein the vaccine also comprises one or more cytokines.

7. The method of claim 2, wherein the vaccine comprises xenoexpressed CD20 antigen, expressed in insect cells.

8. The method of claim 1, wherein the step of administering is achieved by immunization with liposomes comprising purified xenogeneic or xenoexpressed CD20.

9. The method according to claim 1, wherein the xenogeneic or xenoexpressed CD20 antigen is a murine CD20 antigen.

10. The method of claim 1, wherein the step of administering is achieved by immunization with DNA encoding a xenogeneic CD20 antigen.

11. The method of claim 10, wherein the DNA immunization is achieved by immunization with liposomes comprising DNA encoding the xenogeneic CD20 antigen.

12. The method of claim 10, wherein the DNA immunization is achieved by immunization with gold particles coated with DNA encoding the xenogeneic CD20 antigen.

13. A method for stimulating an immune response to a tissue expressing CD20 in a subject individual of a first species, comprising removing blood or bone marrow-derived cells from the subject individual, administering to the blood or bone marrow-derived cells an immunologically-effective amount of DNA encoding a xenogeneic CD20 antigen derived from a second species different from the first species, and reintroducing the treated cells back into the subject individual.

14. The method of claim 13, wherein the step of administering is selected from the group consisting of liposomal transfection, particle bombardment and viral infection.

15. The method of claim 1, wherein the immune response is a cellular or humoral response.

16. The method of claim 15, wherein the amount of xenogeneic or xenoexpressed CD20 antigen is sufficient to provide immunoprotection against growth of tumors expressing CD20.

17. The method of claim 1, wherein the amount of xenogeneic or xenoexpressed CD20 antigen is sufficient to provide immunoprotection against growth of tumors expressing CD20.

18. The method of claim 10, wherein the DNA encoding the CD20 antigen is an expression vector encoding the CD20 antigen.

19. The method of claim 1, wherein the step of administering is achieved by immunization with a construct comprising DNA encoding a xenogeneic CD20 antigen, said construct resulting in expression of the xenogeneic CD20 antigen in the subject individual.

20. The method of claim 1, wherein the subject individual has lymphoma or leukemia.

21. The method of claim 20, wherein the step of administering is achieved by immunization with a construct comprising DNA encoding a xenogeneic CD20 antigen, said construct resulting in expression of the xenogeneic CD20 antigen in the subject individual.

* * * * *

SEQUENCE LISTING

<160> NUMBER OF SEQ ID NOS: 15

<210> SEQ ID NO 1
<211> LENGTH: 26
<212> TYPE: DNA
<213> ORGANISM: human

<400> SEQUENCE: 1
atggatcctg gaggaaatgc tgagag    26

<210> SEQ ID NO 2
<211> LENGTH: 26
<212> TYPE: DNA
<213> ORGANISM: human

<400> SEQUENCE: 2
ggtctagatg gtgcgtatgt gcagag    26

<210> SEQ ID NO 3
<211> LENGTH: 34
<212> TYPE: DNA
<213> ORGANISM: mouse

<400> SEQUENCE: 3
aaggatccag tacactgtag ctatcttcaa gtac    34

<210> SEQ ID NO 4
<211> LENGTH: 28
<212> TYPE: DNA
<213> ORGANISM: mouse

<400> SEQUENCE: 4
cctctagaag agtttaagga gcgatctc    28

<210> SEQ ID NO 5
<211> LENGTH: 6046
<212> TYPE: DNA
<213> ORGANISM: artificial
<220> FEATURE:
<223> OTHER INFORMATION: pCR3-hCD20

<400> SEQUENCE: 5
gcgcgcgttg acattgatta ttgactagtt attaatagta atcaattacg gggtcattag    60
ttcatagccc atatatggag ttccgcgtta cataacttac ggtaaatggc ccgcctggct    120
gaccgcccaa cgacccccgc ccattgacgt caataatgac gtatgttccc atagtaacgc    180
```

```
caatagggac tttccattga cgtcaatggg tggactattt acggtaaact gcccacttgg    240
cagtacatca agtgtatcat atgccaagta cgcccctat tgacgtcaat gacggtaaat     300
ggcccgcctg gcattatgcc cagtacatga ccttatggga ctttcctact tggcagtaca   360
tctacgtatt agtcatcgct attaccatgg tgatgcggtt ttggcagtac atcaatgggc   420
gtggatagcg gtttgactca cggggatttc caagtctcca ccccattgac gtcaatggga   480
gtttgttttg gcaccaaaat caacgggact ttccaaaatg tcgtaacaac tccgcccat    540 tgacgcaaat gggcggtagg cgtgtacggt gggaggtcta taagcaga gctctctggc    600 taactagaga acccactgct tactggctta tcgaaattaa tacgactcac tatagggaga  660
cccaagcttg gtaccgagct cggatccaag cattcagatg catgacacaa ggtaagactg   720
ccaaaaatct tgttcttgct ctcctcattt tgttatttgt tttattttta ggagttttga   780
gagcaaaatg acaacaccca gaaattcagt aaatgggact ttcccggcag agccaatgaa   840 aggcccatt gctatgcaat ctggtccaaa accactcttc aggaggatgt cttcactggt    900
gggccccacg caaagcttct tcatgaggga atctaagact ttggggggctg tccagattat  960 gaatgggctc ttccacattg ccctggggggg tcttctgatg atcccagcag ggatctatgc 1020
acccatctgt gtgactgtgt ggtaccctct ctggggaggc attatgtata ttatttccgg  1080
atcactcttg gcagcaacgg agaaaaactc taggaagtgt ttggtcaaag gaaaaatgat  1140
aatgaattca ttgagcctct ttgctgccat ttctggaatg attctttcaa tcatggacat  1200
acttaatatt aaaattttccc atttttttaaa aatggagagt ctgaattta ttagagctca  1260 cacaccatat attaacatat acaactgtga accagctaat ccctctgaga aaaactcccc   1320
atctacccaa tactgttaca gcatacaatc tctgttcttg ggcattttgt cagtgatgct   1380
gatcttgtcc ttcttccagg aacttgtaat agctggcatc gttgagaatg aatggaaaag   1440
aacgtgctcc agacccaaat ctaacatagt tctcctgtca gcagaagaaa aaaaagaaca   1500
gactattgaa ataaaagaag aagtggttgg gctaactgaa acatcttccc aaccaaagaa   1560
tgaagaagac attgaaatta ttccaatcca agaagaggaa gaagaagaaa cagagacgaa   1620 cttttccagaa cctccccaag atcaggaatc ctcaccaata gaaaatgaca gctctcctta   1680
agtgatttct tctgttttct gtttcctttt ttaaacatta gtgttcatag cttccaagag   1740
acaggtctag agggccctat tctatagtgt cacctaaatg ctagagctcg ctgatcagcc   1800
tcgactgtgc cttctagttg ccagccatct gttgtttgcc cctcccccgt gccttccttg   1860
accctggaag gtgccactcc cactgtcctt tcctaataaa atgaggaaat tgcatcgcat   1920
tgtctgagta ggtgtcattc tattctgggg ggtgggggtgg ggcaggacag caaggggggag  1980 gattgggaag acaatagcag gcatgctggg gatgcggtgg gctctatggc ttctgaggcg   2040
gaaagaacca gtggcggtaa tacggttatc cacagaatca ggggataacg caggaaagaa  2100
catgtgagca aaaggccagc aaaaggccag gaaccgtaaa aaggccgcgt tgctggcgtt   2160
tttccatagg ctccgccccc ctgacgagca tcacaaaaat cgacgctcaa gtcagaggtg  2220
gcgaaacccg acaggactat aaagatacca ggcgtttccc cctggaagct ccctcgtgcg  2280
ctctcctgtt ccgaccctgc cgcttaccgg atacctgtcc gcctttctcc cttcgggaag  2340
cgtggcgctt tctcatagct cacgctgtag gtatctcagt tcggtgtagg tcgttcgctc  2400
caagctgggc tgtgtgcacg aaccccccgt tcagcccgac cgctgcgcct tatccggtaa  2460
ctatcgtctt gagtccaacc cggtaagaca cgacttatcg ccactggcag cagccactgg  2520
taacaggatt agcagagcga ggtatgtagg cggtgctaca gagttcttga agtggtggcc  2580
```

```
taactacggc tacactagaa ggacagtatt tggtatctgc gctctgctga agccagttac    2640
cttcggaaaa agagttggta gctcttgatc cggcaaacaa accaccgctg gtagcggtgg    2700
ttttttttgtt tgcaagcagc agattacgcg cagaaaaaaa ggatctcaag aagatccttt    2760
gatcttttct acggggtctg acgctcagtg gaacgaaaac tcacgttaag ggattttggt    2820
catgagatta tcaaaaagga tcttcaccta gatccttttta aattaaaaat gaagttttaa    2880
atcaatctaa agtatatatg agtaacctga ggctatggca gggcctgccg ccccgacgtt    2940
ggctgcgagc cctgggcctt cacccgaact tgggggggtgg ggtgggaaa aggaagaaac    3000
gcgggcgtat tggccccaat ggggtctcgg tggggtatcg acagagtgcc agccctggga    3060
ccgaaccccg cgtttatgaa caaacgaccc aacaccgtgc gttttattct gtcttttat     3120
tgccgtcata gcgcgggttc cttccggtat tgtctccttc cgtgtttcag ttagcctccc    3180
cctagggtgg gcgaagaact ccagcatgag atccccgcgc tggaggatca tccagccggc    3240
gtcccggaaa acgattccga agcccaacct ttcatagaag gcggcggtgg aatcgaaatc    3300
tcgtgatggc aggttgggcg tcgcttggtc ggtcatttcg aaccccagag tcccgctcag    3360
aagaactcgt caagaaggcg atagaaggcg atgcgctgcg aatcgggagc ggcgataccg    3420
taaagcacga ggaagcggtc agcccattcg ccgccaagct cttcagcaat atcacgggta    3480
gccaacgcta tgtcctgata gcggtccgcc acacccagcc ggccacagtc gatgaatcca    3540
gaaaagcggc cattttccac catgatattc ggcaagcagg catcgccatg ggtcacgacg    3600
agatcctcgc cgtcgggcat gctcgccttg agcctggcga acagttcggc tggcgcgagc    3660
ccctgatgct cttgatcatc ctgatcgaca agaccggctt ccatccgagt acgtgctcgc    3720
tcgatgcgat gtttcgcttg gtggtcgaat gggcaggtag ccggatcaag cgtatgcagc    3780
cgccgcattg catcagccat gatggatact ttctcggcag gagcaaggtg agatgacagg    3840
agatcctgcc ccggcacttc gcccaatagc agccagtccc ttcccgcttc agtgacaacg    3900
tcgagcacag ctgcgcaagg aacgcccgtc gtggccagcc acgatagccg cgctgcctcg    3960
tcttgcagtt cattcagggc accggacagg tcggtcttga caaaaagaac cgggcgcccc    4020
tgcgctgaca gccggaacac ggcggcatca gagcagccga ttgtctgttg tgcccagtca    4080
tagccgaata gcctctccac ccaagcggcc ggagaacctg cgtgcaatcc atcttgttca    4140
atcatgcgaa acgatcctca tcctgtctct tgatcgatct ttgcaaaagc ctaggcctcc    4200
aaaaaagcct cctcactact tctggaatag ctcagaggcc gaggcggcct cggcctctgc    4260
ataaataaaa aaaattagtc agccatgggg cggagaatgg gcggaactgg gcggagttag    4320
gggcgggatg ggcggagtta ggggcgggac tatggttgct gactaattga gatgcatgct    4380
ttgcatactt ctgcctgctg gggagcctgg ggactttcca cacctggttg ctgactaatt    4440
gagatgcatg ctttgcatac ttctgcctgc tggggagcct ggggactttc cacaccctaa    4500
ctgacacaca ttccacagct ggttctttcc gcctcaggac tcttcctttt tcaataaatc    4560
aatctaaagt atatatgagt aaacttggtc tgacagttac caatgcttaa tcagtgaggc    4620
acctatctca gcgatctgtc tatttcgttc atccatagtt gcctgactcc ccgtcgtgta    4680
gataactacg atacgggagg gcttaccatc tggccccagt gctgcaatga taccgcgaga    4740
cccacgctca ccggctccag atttatcagc aataaaccag ccagccggaa gggccgagcg    4800
cagaagtggt cctgcaactt tatccgcctc catccagtct attaattgtt gccgggaagc    4860
tagagtaagt agttcgccag ttaatagttt gcgcaacgtt gttgccattg ctacaggcat    4920
cgtggtgtca cgctcgtcgt ttggtatggc ttcattcagc tccggttccc aacgatcaag    4980
```

```
gcgagttaca tgatccccca tgttgtgcaa aaaagcggtt agctccttcg gtcctccgat    5040
cgttgtcaga agtaagttgg ccgcagtgtt atcactcatg gttatggcag cactgcataa    5100
ttctcttact gtcatgccat ccgtaagatg cttttctgtg actggtgagt actcaaccaa    5160
gtcattctga aatagtgta tgcggcgacc gagttgctct tgcccggcgt caatacggga     5220
taataccgcg ccacatagca gaactttaaa agtgctcatc attggaaaac gttcttcggg    5280
gcgaaaactc tcaaggatct taccgctgtt gagatccagt tcgatgtaac ccactcgtgc    5340
acccaactga tcttcagcat cttttacttt caccagcgtt tctgggtgag caaaaacagg    5400
aaggcaaaat gccgcaaaaa agggaataag ggcgacacgg aaatgttgaa tactcatact    5460 cttcctttt caatattatt gaagcattta tcagggttat tgtctcatga gcggatacat     5520
atttgaatgt atttagaaaa ataaacaaat aggggttccg cgcacatttc cccgaaaagt    5580
gccacctgac gcgcctgta gcggcgcatt aagcgcggcg ggtgtggtgg ttacgcgcag    5640
cgtgaccgct acacttgcca gcgccctagc gcccgctcct ttcgctttct tcccttcctt    5700
tctcgccacg ttcgccggct ttccccgtca gctctaaat cggggctcc ctttagggtt      5760 ccgatttagt gctttacggc acctcgaccc caaaaaactt gattagggtg atggttcacg    5820
tagtgggcca tcgccctgat agacggtttt tcgccctttg acgttggagt ccacgttctt    5880
taatagtgga ctcttgttcc aaactggaac aacactcaac cctatctcgg tctattcttt    5940
tgatttataa gggattttgc cgatttcggc ctattggtta aaaatgagc tgatttaaca    6000 aaaatttaac gcgaatttta acaaaatatt aacgcttaca atttac                  6046

<210> SEQ ID NO 6
<211> LENGTH: 5996
<212> TYPE: DNA
<213> ORGANISM: artificial
<220> FEATURE:
<223> OTHER INFORMATION: pCR3-mCD20

<400> SEQUENCE: 6
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgacccccgc ccattgacgt caataatgac gtatgttccc atagtaacgc     180
caatagggac tttccattga cgtcaatggg tggactattt acggtaaact gcccacttgg     240
cagtacatca agtgtatcat atgccaagta cgccccctat tgacgtcaat gacggtaaat     300
ggcccgcctg gcattatgcc cagtacatga cctattggga cttcctact tggcagtaca     360 tctacgtatt agtcatcgct attaccatgg tgatgcggtt ttggcagtac atcaatgggc     420
gtggatagcg gtttgactca cggggatttc caagtctcca ccccattgac gtcaatggga    480
gtttgttttg gcaccaaaat caacgggact ttccaaaatg tcgtaacaac tccgccccat     540
tgacgcaaat gggcggtagg cgtgtacggt gggaggtcta taagcagag ctctctggc      600 taactagaga acccactgct tactggctta tcgaaattaa tacgactcac tatagggaga    660
cccaagcttg gtaccgagct cggatccagt acactgtagc tatcttcaag tacttgagat    720
agaagaggcc aactgatctc agctgtgagt ggctaatttg gcccttaagc cttggagcct   780
tggagccttg agacccagg cgtttgaaaa ctcaatgagt ggacctttcc cagcagagcc      840
tacaaaaggt cccctcgcca tgcaacctgc tccaaaagtg aacctcaaaa ggacatcttc    900
actggtgggc cccacacaaa gcttcttcat gagggaatca aaggctttgg gggctgtcca   960
aatcatgaat ggcctcttcc atattaccct gggggactg ctgatgatcc ccacagggt     1020
```

```
cttcgcaccc atctgtttga gtgtatggta ccctctctgg ggaggcatta tgtacattat    1080
ttcaggatca ctcctggcag ctgcagcaga aaaaacctcc aggaagagtt tggtcaaagc    1140
aaaagtgata atgagctctc taagcctctt tgctgccatt tctggaataa ttctttcaat    1200
catggacata cttaacatga cactttctca ttttttaaaa atgagaagac tggagcttat    1260
tcaaacttcc aagccgtatg ttgatatcta cgactgtgaa ccatctaatt cctcagagaa    1320
aaactcccca tctacacagt actgtaacag cattcagtct gtgttcttgg cattctgtc     1380 ggcgatgctg atctctgcct tcttccagaa acttgtgaca gctggtattg tggagaatga    1440
gtggaaaaga atgtgtacca gatccaaatc taatgtggtt ctgctgtcag ctggagaaaa    1500
aaatgagcag acgattaaaa tgaaagaaga aatcattgag ctaagtggag tatcttccca    1560
accaaagaat gaagaggaaa ttgaaattat tccagtgcag gaggaagaag aagaagaagc    1620
agaaataaat tttccagcac ctccccaaga gcaggaatcc ttgccagtgg aaaatgagat    1680
cgctccttaa actcttctag agggcccat tctatagtgt cacctaaatg ctagagctcg    1740
ctgatcagcc tcgactgtgc cttctagttg ccagccatct gttgtttgcc cctcccccgt    1800
gccttccttg accctggaag gtgccactcc cactgtcctt tcctaataaa atgaggaaat    1860
tgcatcgcat tgtctgagta ggtgtcattc tattctgggg ggtggggtgg ggcaggacag    1920
caagggggag gattgggaag acaatagcag gcatgctggg gatgcggtgg gctctatggc    1980
ttctgaggcg gaaagaacca gtggcggtaa tacggttatc cacagaatca ggggataacg    2040
caggaaagaa catgtgagca aaaggccagc aaaaggccag gaaccgtaaa aaggccgcgt    2100
tgctggcgtt tttccatagg ctccgccccc ctgacgagca tcacaaaaat cgacgctcaa    2160
gtcagaggtg gcgaaacccg acaggactat aaagatacca ggcgtttccc cctggaagct    2220
ccctcgtgcg ctctcctgtt ccgaccctgc cgcttaccgg atacctgtcc gcctttctcc    2280
cttcgggaag cgtggcgctt tctcatagct cacgctgtag gtatctcagt tcggtgtagg    2340
tcgttcgctc caagctgggc tgtgtgcacg aaccccccgt tcagcccgac cgctgcgcct    2400
tatccggtaa ctatcgtctt gagtccaacc cggtaagaca cgacttatcg ccactggcag    2460
cagccactgg taacaggatt agcagagcga ggtatgtagg cggtgctaca gagttcttga    2520
agtggtggcc taactacggc tacactagaa ggacagtatt tggtatctgc gctctgctga    2580
agccagttac cttcggaaaa agagttggta gctcttgatc cggcaaacaa accaccgctg    2640
gtagcggtgg tttttttgtt tgcaagcagc agattacgcg cagaaaaaaa ggatctcaag    2700
aagatccttt gatcttttct acggggtctg acgctcagtg gaacgaaaac tcacgttaag    2760
ggattttggt catgagatta tcaaaaagga tcttcaccta gatcctttta aattaaaaat    2820
gaagttttaa atcaatctaa agtatatatg agtaacctga gctatggca gggcctgccg    2880 ccccgacgtt ggctgcgagc cctgggcctt cacccgaact ggggggtgg ggtggggaaa    2940 aggaagaaac gcgggcgtat tggccccaat ggggtctcgg tggggtatcg acagagtgcc    3000
agccctggga ccgaacccg cgtttatgaa caaacgaccc acaccgtgc gttttattct    3060 gtcttttat tgccgtcata gcgcgggttc cttccggtat tgtctccttc cgtgtttcag    3120
ttagcctccc cctagggtgg gcgaagaact ccagcatgag atcccgcgc tggaggatca    3180 tccagccggc gtcccggaaa acgattccga agcccaacct ttcatagaag gcggcggtgg    3240
aatcgaaatc tcgtgatggc aggttgggcg tcgcttggtc ggtcatttcg aaccccagag    3300 tccccgctcag aagaactcgt caagaaggcg atagaaggcg atgcgctgcg aatcgggagc    3360
ggcgataccg taaagcacga ggaagcggtc agcccattcg ccgccaagct cttcagcaat    3420
```

```
atcacgggta gccaacgcta tgtcctgata gcggtccgcc acacccagcc ggccacagtc    3480
gatgaatcca gaaaagcggc cattttccac catgatattc ggcaagcagg catcgccatg    3540
ggtcacgacg agatcctcgc cgtcgggcat gctcgccttg agcctggcga acagttcggc    3600
tggcgcgagc ccctgatgct cttgatcatc ctgatcgaca agaccggctt ccatccgagt    3660
acgtgctcgc tcgatgcgat gtttcgcttg gtggtcgaat gggcaggtag ccggatcaag    3720
cgtatgcagc cgccgcattg catcagccat gatggatact ttctcggcag gagcaaggtg    3780
agatgacagg agatcctgcc ccggcacttc gcccaatagc agccagtccc ttcccgcttc    3840
agtgacaacg tcgagcacag ctgcgcaagg aacgcccgtc gtggccagcc acgatagccg    3900
cgctgcctcg tcttgcagtt cattcagggc accggacagg tcggtcttga caaaaagaac    3960
cgggcgcccc tgcgctgaca gccggaacac ggcggcatca gagcagccga ttgtctgttg    4020
tgcccagtca tagccgaata gcctctccac ccaagcggcc ggagaacctg cgtgcaatcc    4080
atcttgttca atcatgcgaa acgatcctca tcctgtctct tgatcgatct ttgcaaaagc    4140
ctaggcctcc aaaaaagcct cctcactact tctggaatag ctcagaggcc gaggcggcct    4200
cggcctctgc ataaataaaa aaaattagtc agccatgggg cggagaatgg gcggaactgg    4260
gcggagttag gggcgggatg gcggagtta ggggcgggac tatggttgct gactaattga    4320
gatgcatgct ttgcatactt ctgcctgctg gggagcctgg ggactttcca cacctggttg    4380
ctgactaatt gagatgcatg cttttgcatac ttctgcctgc tggggagcct ggggactttc    4440
cacaccctaa ctgacacaca ttccacagct ggttctttcc gcctcaggac tcttccttt    4500 tcaataaatc aatctaaagt atatatgagt aaacttggtc tgacagttac caatgcttaa    4560
tcagtgaggc acctatctca gcgatctgtc tatttcgttc atccatagtt gcctgactcc    4620
ccgtcgtgta gataactacg atacgggagg gcttaccatc tggccccagt gctgcaatga    4680
taccgcgaga cccacgctca ccggctccag atttatcagc aataaaccag ccagccggaa    4740
gggccgagcg cagaagtggt cctgcaactt tatccgcctc catccagtct attaattgtt    4800
gccgggaagc tagagtaagt agttcgccag ttaatagttt gcgcaacgtt gttgccattg    4860
ctacaggcat cgtggtgtca cgctcgtcgt ttggtatggc ttcattcagc tccggttccc    4920
aacgatcaag gcgagttaca tgatccccca tgttgtgcaa aaaagcggtt agctccttcg    4980
gtcctccgat cgttgtcaga agtaagttgg ccgcagtgtt atcactcatg gttatggcag    5040
cactgcataa ttctcttact gtcatgccat ccgtaagatg cttttctgtg actggtgagt    5100
actcaaccaa gtcattctga gaatagtgta tgcggcgacc gagttgctct tgcccggcgt    5160
caatacggga taataccgcg ccacatagca gaactttaaa agtgctcatc attggaaaac    5220
gttcttcggg gcgaaaactc tcaaggatct taccgctgtt gagatccagt tcgatgtaac    5280
ccactcgtgc acccaactga tcttcagcat cttttacttt caccagcgtt tctgggtgag    5340
caaaaacagg aaggcaaaat gccgcaaaaa agggaataag ggcgacacgg aaatgttgaa    5400
tactcatact cttcctttt caatattatt gaagcattta tcagggttat tgtctcatga    5460
gcggatacat atttgaatgt atttagaaaa ataaacaaat aggggttccg cgcacatttc    5520
cccgaaaagt gccacctgac gcgcctgta gcggcgcatt aagcgcggcg ggtgtggtgg    5580
ttacgcgcag cgtgaccgct acacttgcca gcgccctagc gcccgctcct ttcgctttct    5640
tcccttcctt tctcgccacg ttcgccggct ttccccgtca agctctaaat cggggggctcc    5700 ctttagggtt ccgatttagt gctttacggc acctcgaccc caaaaaactt gattagggtg    5760
atggttcacg tagtgggcca tcgccctgat agacggtttt tcgccctttg acgttggagt    5820
```

```
ccacgttctt taatagtgga ctcttgttcc aaactggaac aacactcaac cctatctcgg    5880
tctattcttt tgatttataa gggattttgc cgatttcggc ctattggtta aaaaatgagc    5940
tgatttaaca aaaatttaac gcgaattta acaaaatatt aacgcttaca atttac         5996
```

```
<210> SEQ ID NO 7
<211> LENGTH: 46
<212> TYPE: DNA
<213> ORGANISM: artificial
<220> FEATURE:
<223> OTHER INFORMATION: primer

<400> SEQUENCE: 7
ctagctgcag tgtgcagcgc ctcccatttt ttaaaaatgg agagtc                    46

<210> SEQ ID NO 8
<211> LENGTH: 33
<212> TYPE: DNA
<213> ORGANISM: artificial
<220> FEATURE:
<223> OTHER INFORMATION: primer

<400> SEQUENCE: 8
tgctcgagtc aacagtattg ggtagatggg gag                                  33

<210> SEQ ID NO 9
<211> LENGTH: 44
<212> TYPE: PRT
<213> ORGANISM: human

<400> SEQUENCE: 9

Lys Ile Ser His Phe Leu Lys Met Glu Ser Leu Asn Phe Ile Arg Ala
1               5                   10                  15

His Thr Pro Tyr Ile Asn Ile Tyr Asn Cys Glu Pro Ala Asn Pro Ser
            20                  25                  30

Glu Lys Asn Ser Pro Ser Thr Gln Tyr Cys Tyr Ser
        35                  40

<210> SEQ ID NO 10
<211> LENGTH: 46
<212> TYPE: DNA
<213> ORGANISM: artificial
<220> FEATURE:
<223> OTHER INFORMATION: primer

<400> SEQUENCE: 10
ctagctgcag tgtgcagcgc ctctcatttt ttaaaaatga gaagac                    46

<210> SEQ ID NO 11
<211> LENGTH: 33
<212> TYPE: DNA
<213> ORGANISM: artificial
<220> FEATURE:
<223> OTHER INFORMATION: primer

<400> SEQUENCE: 11
tgctcgagtc aacagtactg tgtagatggg gag                                  33

<210> SEQ ID NO 12
<211> LENGTH: 40
<212> TYPE: PRT
<213> ORGANISM: mouse
```

<400> SEQUENCE: 12

```
Ser His Phe Leu Lys Met Arg Arg Leu Glu Leu Ile Gln Thr Ser Lys
1               5                   10                  15

Pro Tyr Val Asp Ile Tyr Asp Cys Glu Pro Ser Asn Ser Ser Glu Lys
            20                  25                  30

Asn Ser Pro Ser Thr Gln Tyr Cys
            35                  40
```

<210> SEQ ID NO 13
<211> LENGTH: 5178
<212> TYPE: DNA
<213> ORGANISM: artificial
<220> FEATURE:
<223> OTHER INFORMATION: pNeris-H8

<400> SEQUENCE: 13

| | | | | | |
|---|---|---|---|---|---|
| gcgcgcgttg | acattgatta | ttgactagtt | attaatagta | atcaattacg | gggtcattag | 60 |
| ttcatagccc | atatatggag | ttccgcgtta | cataacttac | ggtaaatggc | ccgcctggct | 120 |
| gaccgcccaa | cgaccccgc | ccattgacgt | caataatgac | gtatgttccc | atagtaacgc | 180 |
| caatagggac | tttccattga | cgtcaatggg | tggactattt | acggtaaact | gcccacttgg | 240 |
| cagtacatca | agtgtatcat | atgccaagta | cgccccctat | tgacgtcaat | gacggtaaat | 300 |
| ggcccgcctg | gcattatgcc | cagtacatga | ccttatggga | ctttcctact | tggcagtaca | 360 |
| tctacgtatt | agtcatcgct | attaccatgg | tgatgcggtt | ttggcagtac | atcaatgggc | 420 |
| gtggatagcg | gtttgactca | cggggatttc | caagtctcca | ccccattgac | gtcaatggga | 480 |
| gtttgttttg | gcaccaaaat | caacgggact | ttccaaaatg | tcgtaacaac | tccgccccat | 540 |
| tgacgcaaat | gggcggtagg | cgtgtacggt | gggaggtcta | tataagcaga | gctctctggc | 600 |
| taactagaga | acccactgct | tactggctta | tcgaaattaa | tacgactcac | tatagggaga | 660 |
| cccaagcttg | gtaccgagct | cggatccacc | atgagataca | tgatcctggg | cctgctggcc | 720 |
| ctggctgcag | tgtgcagcgc | ctcccatttt | ttaaaaatgg | agagtctgaa | ttttattaga | 780 |
| gctcacacac | catatattaa | catatacaac | tgtgaaccag | ctaatccctc | tgagaaaaac | 840 |
| tccccatcta | cccaatactg | ttcatctcga | gcatgcatct | agagggccct | attctatagt | 900 |
| gtcacctaaa | tgctagagct | cgctgatcag | cctcgactgt | gccttctagt | tgccagccat | 960 |
| ctgttgtttg | cccctccccc | gtgccttcct | tgaccctgga | aggtgccact | cccactgtcc | 1020 |
| tttcctaata | aaatgaggaa | attgcatcgc | attgtctgag | taggtgtcat | tctattctgg | 1080 |
| ggggtggggt | ggggcaggac | agcaagggg | aggattggga | agacaatagc | aggcatgctg | 1140 |
| gggatgcggt | gggctctatg | gcttctgagg | cggaaagaac | cagtggcggt | aatacggtta | 1200 |
| tccacagaat | caggggataa | cgcaggaaag | aacatgtgag | caaaaggcca | gcaaaaggcc | 1260 |
| aggaaccgta | aaaaggccgc | gttgctggcg | tttttccata | ggctccgccc | ccctgacgag | 1320 |
| catcacaaaa | atcgacgctc | aagtcagagg | tggcgaaacc | cgacaggact | ataaagatac | 1380 |
| caggcgtttc | ccctggaag | ctccctcgtg | cgctctcctg | ttccgaccct | gccgcttacc | 1440 |
| ggatacctgt | ccgcctttct | cccttcggga | agcgtggcgc | tttctcatag | ctcacgctgt | 1500 |
| aggtatctca | gttcggtgta | ggtcgttcgc | tccaagctgg | gctgtgtgca | cgaaccccc | 1560 |
| gttcagcccg | accgctgcgc | cttatccggt | aactatcgtc | ttgagtccaa | cccggtaaga | 1620 |
| cacgacttat | cgccactggc | agcagccact | ggtaacagga | ttagcagagc | gaggtatgta | 1680 |
| ggcggtgcta | cagagttctt | gaagtggtgg | cctaactacg | gctacactag | aaggacagta | 1740 |
| tttggtatct | gcgctctgct | gaagccagtt | accttcggaa | aaagagttgg | tagctcttga | 1800 |

-continued

```
tccggcaaac aaaccaccgc tggtagcggt ggttttttg tttgcaagca gcagattacg    1860
cgcagaaaaa aaggatctca agaagatcct ttgatctttt ctacgggtc tgacgctcag    1920
tggaacgaaa actcacgtta agggattttg gtcatgagat tatcaaaaag gatcttcacc   1980
tagatccttt taaattaaaa atgaagtttt aaatcaatct aaagtatata tgagtaacct   2040
gaggctatgg cagggcctgc cgccccgacg ttggctgcga gccctgggcc ttcacccgaa   2100
cttgggggt gggtggga aaggaagaa acgcgggcgt attggcccca atggggtctc       2160
ggtggggtat cgacagagtg ccagccctgg gaccgaaccc cgcgtttatg aacaaacgac   2220
ccaacaccgt gcgttttatt ctgtcttttt attgccgtca tagcgcgggt tccttccggt   2280
attgtctcct tccgtgtttc agttagcctc ccctagggt gggcgaagaa ctccagcatg    2340
agatccccgc gctggaggat catccagccg gcgtcccgga aaacgattcc gaagcccaac   2400
cttcataga aggcggcggt ggaatcgaaa tctcgtgatg gcaggttggg cgtcgcttgg    2460
tcggtcattt cgaaccccag agtcccgctc agaagaactc gtcaagaagg cgatagaagg   2520
cgatgcgctg cgaatcggga gcggcgatac cgtaaagcac gaggaagcgg tcagcccatt   2580
cgccgccaag ctcttcagca atatcacggg tagccaacgc tatgtcctga tagcggtccg   2640
ccacacccag ccggccacag tcgatgaatc cagaaaagcg gccattttcc accatgatat   2700
tcggcaagca ggcatcgcca tgggtcacga cgagatcctc gccgtcgggc atgctcgcct   2760
tgagcctggc gaacagttcg gctggcgcga gcccctgatg ctcttgatca tcctgatcga   2820
caagaccggc ttccatccga gtacgtgctc gctcgatgcg atgtttcgct tggtggtcga   2880
atgggcaggt agccggatca agcgtatgca gccgccgcat tgcatcagcc atgatggata   2940
ctttctcggc aggagcaagg tgagatgaca ggagatcctg ccccggcact tcgcccaata   3000
gcagccagtc ccttcccgct tcagtgacaa cgtcgagcac agctgcgcaa ggaacgcccg   3060
tcgtggccag ccacgatagc cgcgctgcct cgtcttgcag ttcattcagg caccggaca    3120
ggtcggtctt gacaaaaaga accgggcgcc cctgcgctga cagccggaac acggcggcat   3180
cagagcagcc gattgtctgt tgtgcccagt catagccgaa tagcctctcc acccaagcgg   3240
ccggagaacc tgcgtgcaat ccatcttgtt caatcatgcg aaacgatcct catcctgtct   3300
cttgatcgat cttttgcaaaa gcctaggcct ccaaaaaagc ctcctcacta cttctggaat   3360
agctcagagg ccgaggcggc ctcggcctct gcataaataa aaaaaattag tcagccatgg   3420
ggcggagaat gggcggaact gggcggagtt aggggcggga tgggcggagt taggggcggg   3480
actatggttg ctgactaatt gagatgcatg ctttgcatac ttctgcctgc tggggagcct   3540
ggggactttc cacacctggt tgctgactaa ttgagatgca tgctttgcat acttctgcct   3600
gctgggagc ctggggactt tccacaccct aactgacaca cattccacag ctggttcttt    3660
ccgcctcagg actcttcctt tttcaataaa tcaatctaaa gtatatatga gtaaacttgg   3720
tctgacagtt accaatgctt aatcagtgag gcacctatct cagcgatctg tctatttcgt   3780
tcatccatag ttgcctgact ccccgtcgtg tagataacta cgatacggga gggcttacca   3840
tctggcccca gtgctgcaat gataccgcga gacccacgct caccggctcc agatttatca   3900
gcaataaacc agccagccgg aagggccgag cgcagaagtg gtcctgcaac tttatccgcc   3960
tccatccagt ctattaattg ttgccgggaa gctagagtaa gtagttcgcc agttaatagt   4020
ttgcgcaacg ttgttgccat tgctacaggc atcgtggtgt cacgctcgtc gtttggtatg   4080
gcttcattca gctccggttc ccaacgatca aggcgagtta catgatcccc catgttgtgc   4140
aaaaaagcgg ttagctcctt cggtcctccg atcgttgtca gaagtaagtt ggccgcagtg   4200
```

```
ttatcactca tggttatggc agcactgcat aattctctta ctgtcatgcc atccgtaaga    4260
tgcttttctg tgactggtga gtactcaacc aagtcattct gagaatagtg tatgcggcga    4320
ccgagttgct cttgcccggc gtcaatacgg gataataccg cgccacatag cagaacttta    4380
aaagtgctca tcattggaaa acgttcttcg gggcgaaaac tctcaaggat cttaccgctg    4440
ttgagatcca gttcgatgta acccactcgt gcacccaact gatcttcagc atcttttact    4500
ttcaccagcg tttctgggtg agcaaaaaca ggaaggcaaa atgccgcaaa aaagggaata    4560
agggcgacac ggaaatgttg aatactcata ctcttccttt ttcaatatta ttgaagcatt    4620
tatcagggtt attgtctcat gagcggatac atatttgaat gtatttagaa aaataaacaa    4680
ataggggttc cgcgcacatt tccccgaaaa gtgccacctg acgcgccctg tagcggcgca    4740
ttaagcgcgg cgggtgtggt ggttacgcgc agcgtgaccg ctacacttgc cagcgcccta    4800
gcgcccgctc ctttcgcttt cttcccttcc tttctcgcca cgttcgccgg ctttccccgt    4860
caagctctaa atcgggggct ccctttaggg ttccgattta gtgctttacg cacctcgac    4920 cccaaaaaac ttgattaggg tgatggttca cgtagtgggc catcgccctg atagacggtt    4980
tttcgccctt tgacgttgga gtccacgttc tttaatagtg gactcttgtt ccaaactgga    5040
acaacactca accctatctc ggtctattct tttgatttat aagggatttt gccgatttcg    5100
gcctattggt taaaaaatga gctgatttaa caaaaattta acgcgaattt taacaaaata    5160
ttaacgctta caatttac                                                 5178

<210> SEQ ID NO 14
<211> LENGTH: 5175
<212> TYPE: DNA
<213> ORGANISM: artificial
<220> FEATURE:
<223> OTHER INFORMATION: pNERIS-M8

<400> SEQUENCE: 14
gcgcgcgttg acattgatta ttgactagtt attaatagta atcaattacg ggtcattag      60 ttcatagccc atatatggag ttccgcgtta cataacttac ggtaaatggc ccgcctggct    120
gaccgcccaa cgacccccgc ccattgacgt caataatgac gtatgttccc atagtaacgc    180
caatagggac tttccattga cgtcaatggg tggactattt acggtaaact gcccacttgg    240
cagtacatca agtgtatcat atgccaagta cgccccctat tgacgtcaat gacggtaaat    300
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta taagcaga gctctctggc      600 taactagaga acccactgct tactggctta tcgaaattaa tacgactcac tatagggaga    660
cccaagcttg gtaccgagct cggatccacc atgagataca tgatcctggg cctgctggcc    720
ctggctgcag tgtgcagcgc ctctcatttt ttaaaaatga aagactgga gcttattcaa    780 acttccaagc cgtatgttga tatctacgac tgtgaaccat ctaattcctc agagaaaaac    840
tccccatcta cacagtactg ttctcgagca tgcatctaga gggcccattt ctatagtgtc    900
acctaaatgc tagagctcgc tgatcagcct cgactgtgcc ttctagttgc cagccatctg    960
ttgtttgccc ctcccccgtg ccttccttga ccctggaagg tgccactccc actgtccttt    1020
cctaataaaa tgaggaaatt gcatcgcatt gtctgagtag gtgtcattct attctggggg    1080
```

```
gtggggtggg gcaggacagc aaggggagg attgggaaga caatagcagg catgctgggg   1140
atgcggtggg ctctatggct tctgaggcgg aaagaaccag tggcggtaat acggttatcc   1200
acagaatcag gggataacgc aggaaagaac atgtgagcaa aaggccagca aaaggccagg   1260
aaccgtaaaa aggccgcgtt gctggcgttt ttccataggc tccgcccccc tgacgagcat   1320
cacaaaaatc gacgctcaag tcagaggtgg cgaaacccga caggactata agataccag    1380 gcgtttcccc ctggaagctc cctcgtgcgc tctcctgttc cgaccctgcc gcttaccgga   1440
tacctgtccg cctttctccc ttcgggaagc gtggcgcttt ctcatagctc acgctgtagg   1500
tatctcagtt cggtgtaggt cgttcgctcc aagctgggct gtgtgcacga accccccgtt   1560
cagcccgacc gctgcgcctt atccggtaac tatcgtcttg agtccaaccc ggtaagacac   1620
gacttatcgc cactggcagc agccactggt aacaggatta gcagagcgag gtatgtaggc   1680
ggtgctacag agttcttgaa gtggtggcct aactacggct acactagaag gacagtattt   1740
ggtatctgcg ctctgctgaa gccagttacc ttcggaaaaa gagttggtag ctcttgatcc   1800
ggcaaacaaa ccaccgctgg tagcggtggt ttttttgttt gcaagcagca gattacgcgc   1860
agaaaaaaag gatctcaaga agatccttg atcttttcta cggggtctga cgctcagtgg    1920
aacgaaaact cacgttaagg gattttggtc atgagattat caaaaaggat cttcacctag   1980
atccttttaa attaaaaatg aagttttaaa tcaatctaaa gtatatatga gtaacctgag   2040
gctatggcag ggcctgccgc cccgacgttg gctgcgagcc ctgggccttc acccgaactt   2100 gggggggtggg gtggggaaaa ggaagaaacg cgggcgtatt ggccccaatg gggtctcggt   2160
ggggtatcga cagagtgcca gccctgggac cgaacccgc gtttatgaac aaacgaccca    2220
acaccgtgcg ttttattctg tctttttatt gccgtcatag cgcgggttcc ttccggtatt   2280
gtctccttcc gtgtttcagt tagcctcccc ctagggtggg cgaagaactc cagcatgaga   2340
tccccgcgct ggaggatcat ccagccggcg tcccggaaaa cgattccgaa gcccaacctt   2400
tcatagaagg cggcggtgga atcgaaatct cgtgatggca ggttgggcgt cgcttggtcg   2460
gtcatttcga accccagagt cccgctcaga agaactcgtc aagaaggcga tagaaggcga   2520
tgcgctgcga atcgggagcg gcgataccgt aaagcacgag gaagcggtca gcccattcgc   2580
cgccaagctc ttcagcaata tcacgggtag ccaacgctat gtcctgatag cggtccgcca   2640
cacccagccg gccacagtcg atgaatccag aaaagcggcc attttccacc atgatattcg   2700
gcaagcaggc atcgccatgg gtcacgacga gatcctcgcc gtcgggcatg ctcgccttga   2760
gcctggcgaa cagttcggct ggcgcgagcc ctgatgctc ttgatcatcc tgatcgacaa    2820
gaccggcttc catccgagta cgtgctcgct cgatgcgatg tttcgcttgg tggtcgaatg   2880
ggcaggtagc cggatcaagc gtatgcagcc gccgcattgc atcagccatg atggatactt   2940
tctcggcagg agcaaggtga gatgacagga gatcctgccc cggcacttcg cccaatagca   3000
gccagtccct tcccgcttca gtgacaacgt cgagcacagc tgcgcaagga acgcccgtcg   3060
tggccagcca cgatagccgc gctgcctcgt cttgcagttc attcagggca ccggacaggt   3120
cggtcttgac aaaaagaacc gggcgcccct gcgctgacag ccggaacacg gcggcatcag   3180
agcagccgat tgtctgttgt gcccagtcat agccgaatag cctctccacc caagcggccg   3240
gagaacctgc gtgcaatcca tcttgttcaa tcatgcgaaa cgatcctcat cctgtctctt   3300
gatcgatctt tgcaaaagcc taggcctcca aaaaagcctc ctcactactt ctggaatagc   3360
tcagaggccg aggcggcctc ggcctctgca taaataaaaa aaattagtca gccatggggc   3420
ggagaatggg cggaactggg cggagttagg ggcgggatgg gcggagttag ggcgggact    3480
```

```
atggttgctg actaattgag atgcatgctt tgcatacttc tgcctgctgg ggagcctggg    3540
gactttccac acctggttgc tgactaattg agatgcatgc tttgcatact tctgcctgct    3600
ggggagcctg gggactttcc acaccctaac tgacacacat tccacagctg gttctttccg    3660
cctcaggact cttcctttt  caataaatca atctaaagta tatatgagta aacttggtct    3720
gacagttacc aatgcttaat cagtgaggca cctatctcag cgatctgtct atttcgttca    3780
tccatagttg cctgactccc cgtcgtgtag ataactacga tacgggaggg cttaccatct    3840
ggccccagtg ctgcaatgat accgcgagac ccacgctcac cggctccaga tttatcagca    3900
ataaaccagc cagccggaag ggccgagcgc agaagtggtc ctgcaacttt atccgcctcc    3960
atccagtcta ttaattgttg ccgggaagct agagtaagta gttcgccagt taatagtttg    4020
cgcaacgttg ttgccattgc tacaggcatc gtggtgtcac gctcgtcgtt tggtatggct    4080
tcattcagct ccggttccca acgatcaagg cgagttacat gatccccat  gttgtgcaaa    4140
aaagcggtta gctccttcgg tcctccgatc gttgtcagaa gtaagttggc cgcagtgtta    4200
tcactcatgg ttatggcagc actgcataat tctcttactg tcatgccatc cgtaagatgc    4260
ttttctgtga ctggtgagta ctcaaccaag tcattctgag aatagtgtat gcggcgaccg    4320
agttgctctt gcccggcgtc aatacgggat aataccgcgc cacatagcag aactttaaaa    4380
gtgctcatca ttggaaaacg ttcttcgggg cgaaaactct caaggatctt accgctgttg    4440
agatccagtt cgatgtaacc cactcgtgca cccaactgat cttcagcatc ttttactttc    4500
accagcgttt ctgggtgagc aaaaacagga aggcaaaatg ccgcaaaaaa gggaataagg    4560
gcgacacgga aatgttgaat actcatactc ttcctttttc aatattattg aagcatttat    4620
cagggttatt gtctcatgag cggatacata tttgaatgta tttagaaaaa taaacaaata    4680
ggggttccgc gcacatttcc ccgaaaagtg ccacctgacg cgccctgtag cggcgcatta    4740
agcgcggcgg gtgtggtggt tacgcgcagc gtgaccgcta cacttgccag cgccctagcg    4800
cccgctcctt tcgctttctt cccttccttt ctcgccacgt tcgccggctt tccccgtcaa    4860
gctctaaatc ggggggctccc tttagggttc cgatttagtg ctttacggca cctcgacccc    4920
aaaaaacttg attagggtga tggttcacgt agtgggccat cgccctgata acggttttt    4980
cgcccttgga cgttggagtc cacgttcttt aatagtggac tcttgttcca aactggaaca    5040
acactcaacc ctatctcggt ctattctttt gatttataag ggattttgcc gatttcggcc    5100
tattggttaa aaaatgagct gatttaacaa aaatttaacg cgaattttaa caaaatatta    5160
acgcttacaa tttac                                                      5175
```

```
<210> SEQ ID NO 15
<211> LENGTH: 28
<212> TYPE: DNA
<213> ORGANISM: artificial
<220> FEATURE:
<223> OTHER INFORMATION: primer

<400> SEQUENCE: 15
cggaattcag agtttaagga gcgatctc                                          28
```